US008927812B2

(12) United States Patent
Schultheiβ

(10) Patent No.: US 8,927,812 B2
(45) Date of Patent: Jan. 6, 2015

(54) METHODS FOR INCREASING THE RESISTANCE OF PLANTS TO FUNGI BY SILENCING THE FUNGAL SMT1-GENE

(75) Inventor: Holger Schultheiβ, Böhl-Iggelheim (DE)

(73) Assignee: BASF Plant Science Company GmbH, Ludwigshafen (DE)

( * ) Notice: Subject to any disclaimer, the term of this patent is extended or adjusted under 35 U.S.C. 154(b) by 211 days.

(21) Appl. No.: 13/514,693

(22) PCT Filed: Dec. 6, 2010

(86) PCT No.: PCT/EP2010/068951
§ 371 (c)(1),
(2), (4) Date: Jun. 8, 2012

(87) PCT Pub. No.: WO2011/066953
PCT Pub. Date: Jun. 16, 2011

(65) Prior Publication Data

US 2012/0246758 A1 Sep. 27, 2012

Related U.S. Application Data

(60) Provisional application No. 61/267,864, filed on Dec. 9, 2009.

(30) Foreign Application Priority Data

Dec. 9, 2009 (EP) .................................... 09178538

(51) Int. Cl.

| | |
|---|---|
| ***C12N 15/82*** | (2006.01) |
| ***C12N 15/00*** | (2006.01) |
| ***C12N 15/14*** | (2006.01) |
| ***A01H 5/00*** | (2006.01) |
| ***C12N 9/10*** | (2006.01) |

(52) U.S. Cl.
CPC ............ *C12N 15/8218* (2013.01); *C12N 9/107* (2013.01); *C12N 15/8282* (2013.01)
USPC ........ 800/301; 435/320.1; 435/419; 800/285; 800/298

(58) Field of Classification Search
None
See application file for complete search history.

(56) References Cited

U.S. PATENT DOCUMENTS 6,225,075 B1 * 5/2001 Bard ............................... 435/15
6,747,137 B1 * 6/2004 Weinstock et al. .......... 536/23.1

FOREIGN PATENT DOCUMENTS

WO WO-98/45457 A1 10/1998
WO WO-2006/047495 A2 5/2006
WO WO-2008/017706 A1 2/2008

OTHER PUBLICATIONS

Chung et al, 2000, Bioorganic & Med. Chem., 8:2475-2486.*
Godoy et al, 2004, Fitopatol. bras., 29: Abstract.*
Ponte et al, 2006, Phytopathology, 96:797-803.*
Carland et al, 2010, Plant Phys., 153:741-756.*
Kaemper, J., et al., "Insights from the Genome of the Biotrophic Fungal Plant Pathogen *Ustilago maydis*", Nature, vol. 444, (2006), pp. 97-101.
Eamens, A., et al., "RAN Silencing in Plants: Yesterday, Today, and Tomorrow", Plant Physiology, vol. 147, (2008), pp. 456-468.
Henderson, I.R., et al., "Dissecting *Arabidopsis thaliana* DICER Function in Small RNA Processing, Gene Silencing and DNA Methylation Patterning", Nature Genetics, vol. 38, No. 6, (2006), pp. 721-725.
"Putative uncharacterized protein", Accession No. Q4P9N1, UniProt Database, Jul. 19, 2005.
Rytter, J.L., et al., "Additional Alternative Hosts of *Phakopsora pachyrhizi*, Causal Agent of Soybean Rust", Plant Disease, vol. 68, No. 9, (1984), pp. 818-819.
Frederick, R. D., et al., "Polymerase Chain Reaction Assays for the Detection and Discrimination of the Soybean Rust Pathogens *Phakopsora pachyrhizi* and *P. meibomiae*", Phytopathology, vol. 92, No. 2, (2002), pp. 217-227.
European Search Report for EP 09178538, search completed Apr. 23, 2010.
International Search Report for PCT/EP2010/068951, mailed Mar. 17, 2011.
International Preliminary Report on Patentability for PCT/EP2010/068951, report dated Jun. 12, 2012.

* cited by examiner

*Primary Examiner* — David H Kruse
*Assistant Examiner* — Jason Deveau Rosen
(74) *Attorney, Agent, or Firm* — Drinker Biddle & Reath LLP

(57) ABSTRACT

The present invention relates to methods for generating or increasing resistance to at least one fungi, in particular soy bean rust, in a plant or a part of a plant by the expression of RNA which is at least partial complementary and/or identical to the STM1-gene, wherein the RNA is capable to provide ds-RNA and/or siRNA and/or miRNA. Moreover, the invention relates to respective plants, parts thereof and vector constructs capable to provide such RNA and the use of such vector constructs to provide fungal resistant plants.

27 Claims, 8 Drawing Sheets

Figure 1 (SEQ-ID-1)

Full-length –sequence of SMT1-gene

```
   1 ATGTCTCCCC CTGATGGTTC ATCCGTGACA GCCACGGAGC TTGCAAAGGC
  51 TGGTGATCTA AGAAACCGAA AAGGTATGGC TCAGTATACC AACTTCTGGA
 101 AAAATGACCA GTCAAAAGAT CCCAAGGCAG ACGGGGAGAG GAGAAAAGAG
 151 CAGTACCAAG ACTTGGTGAA TGGTTACTAT GACTGCGTAA CCGACCTTTA
 201 CGAGTACGGC TGGGGCCAGA ACTTTCATTT TTGTCGTTTT TACAAGGGTG
 251 AAGCCTTTGC CCAGGGAATT GCTCGACATG AACACTACCT TGCGGCGCAG
 301 ATCGGAATTA AGGAGAACAT GAAGGTTCTC GACGTTGGGT GTGGTGTCGG
 351 GGGTCCGGCA AGAGAGATCT GTTGGTTCTC AGACGCAAAC ATCGTCGGGA
 401 TCAACAATAA CATATTCCAG GTCGACCGTG CGATCAAGTA TGCCGCAAAG
 451 GCCGGATTGT CTCACAAGTT GACGTTTGAG AAAGGTAATT TTATGGACAT
 501 GGCCAGTCAG TTTGGCGAAA ATACCTTTGA TGCCGTCTAT GCTATAGAAG
 551 CTACTGTCCA TGCTCCAAAC TGTGAGGGAG TGTACGGAGA GGTTTTTAAG
 601 GTTTTAAAAC CTGGAGGTGT CTTTGGATTT TACGAGTGGT GCTTGACCGA
 651 CAAGTTTAAT GAAAATGATG CCGCTCATCG ACAGATTCGG CATGAAATCG
 701 AGCTTGGAGA TGCGATTCCA GAGCTCCGAA CTATTGAAAG ATCGGCCGAG
 751 GGCTTGAAGG CTGTCGGATT TGAGATCATG AAGTCTGAAG ATCTGGCTAC
 801 CAGGAAGGAT CCACTTCCTT GGTACTACCC TCTCCGTGGT AGCCTTTCGG
 851 AGGCTCAAAC CTTATGGGAT TATGTCACCA TATTCCGCTT GACGACTTTT
 901 GGTAAAGCGT TGGCCTCAAC AGCTGTTAGG GTTATGGAAA CCGTTGGCTT
 951 AGCTCCAAAA GGATCATCTG CTGCAGACAA ATCTCTAAAT ATTGCAGCTT
1001 TATCTCTTGT CAAAGGAGGA GAGACAGGAA TATTTACACC CATGCAATTG
1051 TTCGTCTGCC GCAAGCCCTT TAATAAACTA TAA
```

Figure 2a (SEQ.ID-2)

SMT1-Sequence from Phakopsora pachyrhizi used for primer design and construct generation

```
  1 GACCGCCGAG GACGGCAAGT GACTGTATAC GACTCAGCTG GAGCGAATTG
 51 GAGCTCCACC GCGGTGGCGG TCGCTCTAGA ACTAGTGGAT CCCCCGGGCT
101 GCAGGAATTC GATCCGGCCT TTGCGGCATA CTTGATCGCA CGGTCGACCT
151 GGAATATGTT ATTGTTGATC CCGACGATGT TTGCGTCTGA GAACCAACAG
201 ATCTCTCTTG CCGGACCCCC GACACCACAC CCAACGTCGA GAACCTTCAT
251 GTTCTCCTTA ATTCCGATCT GCGCCGCAAG GTAGTGTTCA TGTCGAGCAA
301 TTCCCTGGGC AAAGGCTTCA CCCTTGTAAA AACGACAAAA ATGAAAGTTC
351 TAGGTTTTTT TACAAAGCGA TTGTAATTTG ATCGCTCAGT CAATCTTCTT
401 CACAAGAGAT AATGATTTTT CAAATGATTT TTTTAACAAT GTGTAACTCA
451 CCTGGCCCCA GCCGTACTCG TAAAGGTCGG TTACGCAGTC ATAGTAACCA
501 TTCACCAAGT CTTGGTACTG CTCTTTTCTC CTCTCCCCGT CTGCCTTGGG
551 ATCTTTTGAC TGGTCATTTT TCCAGAAGTT GGTATACTGA GCCATACCTT
601 TTCGGTTTCT TAGATCACCA GCCTTTGCAA GCTCCGTGGC TGTCACGGAT
651 GAACCATCAG GGGGAGACAT GTTTTAAAGA TGTTTTAAGA CGTATGTATA
701 GATTGAGGAC TGTGTACAGG GAGGATGGGT GAGGTTAGGT GACAGGCGGG
751 ATTGTGGTAT CAGTTGAAGT TCTCTACTGA TTGTAGGATG GATGAGGAAG
801 AGGTAGTACT GGAATTCATG ATCATTATCT GTGTAGATTG AGTTGGTTCT
851 CAGGCAGACC GTATGGTGAT CGAAAAGCCC AAACATTACA ACACTGGTTC
901 CGACGTTGAA CTCTTCATTT AGTTTGAAAT TGAAAGTCAC AGTCAAACCC
951 A
```

Figure 2b (SEQ.ID-3)

```
  1 CCTGGAATAT GTTATTGTTG ATCCCGACGA TGTTTGCGTC TGAGAACCAA
 51 CAGATCTCTC TTGCCGGACC CCCGACACCA CACCCAACGT CGAGAACCTT
101 CATGTTCTCC TTAATTCCGA TCTGCGCCGC AAGGTAGTGT TCATGTCGAG
151 CAATTCCCTG GGCAAAGGCT TCACCCTTGT AAAAACGACA AAAATGAAAG
201 TTCTAGGTTT TTTTACAAAG CGATTGTAAT TTGATCGCTC AGTCAATCTT
251 CTTCACAAGA GATAATGATT TTTCAAATGA TTTTTTTAAC AATGTGTAAC
301 TCACCTG
```

Figure 3

PcUbiquitinPromotor:STMas:spacer:STMsense:terminator (SEQ-ID-4)

aattcgaatccaaaaattacggatatgaatataggcatatccgtatccgaattatccgtttgacagctagcaacgattgtacaattgcttctttaa
aaaaggaagaaagaaagaaagaaaagaatcaacatcagcgttaacaaacggccccgttacggcccaaacggtcatatagagtaac
ggcgttaagcgttgaaagactcctatcgaaatacgtaaccgcaaacgtgtcatagtcagatcccctcttccttcaccgcctcaaacacaaaa
ataatcttctacagcctatatatacaacccccccttctatctctcctttctcacaattcatcatctttctttctctacccccaattttaagaaatcctctct
tctcctcttcattttcaaggtaaatctctctctctctctctctctctgttattccttgttttaattaggtatgtattattgctagtttgttaatctgcttatcttatgt
atgccttatgtgaatatctttatcttgttcatctcatccgtttagaagctataaatttgttgatttgactgtgtatctacacgtggttatgtttatatctaatc
agatatgaatttcttcatattgttgcgtttgtgtgtaccaatccgaaatcgttgatttttttcatttaatcgtgtagctaattgtacgtatacatatggatct
acgtatcaattgttcatctgtttgtgtttgtatgtatacagatctgaaaacatcacttctctcatctgattgtgttgttacatacatagatatagatctgtt
atatcatttttttattaattgtgtatatatatatgtgcatagatctggattacatgattgtgattatttacatgattttgttatttacgtatgtatatatgtaga
tctggactttttggagttgttgacttgattgtatttgtgtgtgtatatgtgtgttctgatcttgatatgttatgtatgtgcagcccggatcaagggcgaatt
cgacccaagtttgtacaaaaaagcaggctggcgcgcccaggtgagttacacattgttaaaaaaatcatttgaaaaatcattatctcttgtgaa
gaagattgactgagcgatcaaattacaatcgctttgtaaaaaaacctagaactttcatttttgtcgtttttacaagggtgaagcctttgcccagg
gaattgctcgacatgaacactaccttgcggcgcagatcggaattaaggagaacatgaaggttctcgacgttgggtgtggtgtcgggggtcc
ggcaagagagatctgttggttctcagacgcaaacatcgtcgggatcaacaataacatattccagggacgtctaaataactaatactccccg
agtctgaaccgctcgatcgaacctcactcaacactgacgagagcgagtcgtctaactcttgcagcctctttgcgtcgtgaaagctctctggat
ccccgagaaactcggataagagactcacagagtagccaccctcggtcacaacgctacaatcgtccaagctcgtaagctcgaagccgaa
gtccagatctgtgctggcgaagtcgatctcggacttaagaacttcctccaaatcgcggtcgcagtcttcaaattcgttagttatttactcgagaa
cagatctctcttgccggacccccgacaccacacccaacgtcgagaaccttcatgttctccttaattccgatctgcgccgcaaggtagtgttcat
gtcgagcaattccctgggcaaaggcttcacccttgtaaaaacgacaaaaatgaaagttctaggtttttttacaaagcgattgtaatttgatcgct
cagtcaatcttcttcacaagagataatgatttttcaaatgatttttttaacaatgtgtaactcacctgcctgcaggggggacccagctttcttgtac
aaagtgggacctaggatcgttcaaacatttggcaataaagtttcttaagattgaatcctgttgccggtcttgcgatgattatcatataatttctgttg
aattacgttaagcatgtaataattaacatgtaatgcatgacgttatttatgagatgggtttttatgattagagtcccgcaattatacatttaatacgc
gatagaaaacaaaatatagcgcgcaaactaggataaattatcgcgcgcggtgtcatctatgttactagatc

Figure 4 (SEQ-ID-5)

```
MSPPDGSSVTATELAKAGDLRNRKGMAQYTNFWKNDQSKDPKADGERRKE  50
QYQDLVNGYYDCVTDLYEYGWGQNFHFCRFYKGEAFAQGIARHEHYLAAQ 100
IGIKENMKVLDVGCGVGGPAREICWFSDANIVGINNNIFQVDRAIKYAAK 150
AGLSHKLTFEKGNFMDMASQFGENTFDAVYAIEATVHAPNCEGVYGEVFK 200
VLKPGGVFGFYEWCLTDKFNENDAAHRQIRHEIELGDAIPELRTIERSAE 250
GLKAVGFEIMKSEDLATRKDPLPWYYPLRGSLSEAQTLWDYVTIFRLTTF 300
GKALASTAVRVMETVGLAPKGSSAADKSLNIAALSLVKGGETGIFTPMQL 350
FVCRKPFNKL*
```

Figure 5

PcUbiquitin-Promotor (SEQ-ID-6)
aattcgaatccaaaaattacggatatgaatataggcatatccgtatccgaattatccgtttgacagctagcaacgattgtacaattgcttctttaa
aaaaggaagaaagaaagaaagaaaagaatcaacatcagcgttaacaaacggccccgttacggcccaaacggtcatatagagtaac
ggcgttaagcgttgaaagactcctatcgaaatacgtaaccgcaaacgtgtcatagtcagatcccctcttccttcaccgcctcaaacacaaaa
ataatcttctacagcctatatatacaacccccccttctatctctcctttctcacaattcatcatctttctttctctacccccaatttaagaaatcctctct
tctcctcttcattttcaaggtaaatctctctctctctctctctctgttattccttgtttaattaggtatgtattattgctagtttgttaatctgcttatcttatgt
atgccttatgtgaatatctttatcttgttcatctcatccgtttagaagctataaatttgttgatttgactgtgtatctacacgtggttatgtttatatctaatc
agatatgaatttcttcatattgttgcgtttgtgtgtaccaatccgaaatcgttgattttttcatttaatcgtgtagctaattgtacgtatacatatggatct
acgtatcaattgttcatctgtttgtgtttgtatgtatacagatctgaaaacatcacttctctcatctgattgtgtgttacatacatagatatagatctgtt
atatcatttttttattaattgtgtatatatatatgtgcatagatctggattacatgattgtgattatttacatgattttgttatttacgtatgtatatatgtaga
tctggacttttggagttgttgacttgattgtatttgtgtgtgtatatgtgtgttctgatcttgatatgttatgtatgtgcag STMantisense (SEQ-ID-7)
caggtgagttacacattgttaaaaaaatcatttgaaaaatcattatctcttgtgaagaagattgactgagcgatcaaattacaatcgctttgtaa
aaaaacctagaactttcatttttgtcgtttttacaagggtgaagcctttgcccagggaattgctcgacatgaacactaccttgcggcgcagatc
ggaattaaggagaacatgaaggttctcgacgttgggtgtggtgtcgggggtccggcaagagagatctgttggttctcagacgcaaacatcg
tcgggatcaacaataacatattccagg Spacer (SEQ-ID-8)
tactccccgagtctgaaccgctcgatcgaacctcactcaacactgacgagagcgagtcgtctaactcttgcagcctctttgcgtcgtgaaag
ctctctggatccccgagaaactcggataagagactcacagagtagccaccctcggtcacaacgctacaatcgtccaagctcgtaagctcg
aagccgaagtccagatctgtgctggcgaagtcgatctcggacttaagaacttcctccaaatcgcggtcgcagtcttcaaattcg STMsense (SEQ-ID-9)
aacagatctctcttgccggacccccgacaccacacccaacgtcgagaaccttcatgttctccttaattccgatctgcgccgcaaggtagtgtt
catgtcgagcaattccctgggcaaaggcttcacccttgtaaaaacgacaaaaatgaaagttctaggtttttttacaaagcgattgtaatttgatc
gctcagtcaatcttcttcacaagagataatgatttttcaaatgatttttttaacaatgtgtaactcacctgc terminator (SEQ-ID-10)
gatcgttcaaacatttggcaataaagtttcttaagattgaatcctgttgccggtcttgcgatgattatcatataatttctgttgaattacgttaagcat
gtaataattaacatgtaatgcatgacgttatttatgagatgggtttttatgattagagtcccgcaattatacatttaatacgcgatagaaaacaaa
atatagcgcgcaaactaggataaattatcgcgcgcggtgtcatctatgttactagatc

Figure 7

- Screening of leaf-backside
- Screening of mature leaves, younger leaves are more susceptible 1 – Very few lesions on young leaves, no yellowing (<5% of leaf surface)

2 – Lesions on 5 – 20 % of leaf surface, no / very little yellowing

3 – Lesions and yellowing on 20 - 40 % of leaf surface

4 – Lesions and yellowing on 40 – 75% of leaf surface

5 – Leaves heavily infected, strong yellowing (>75% of leaf surface)

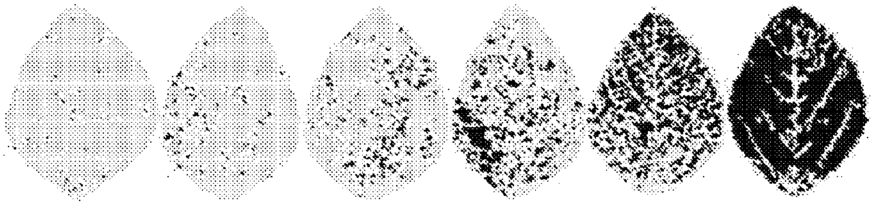

0,6% 2,0% 7,0% 18,0% 42,0% 78,5%

SEQUENCE LISTING

```
<160> NUMBER OF SEQ ID NOS: 14

<210> SEQ ID NO 1
<211> LENGTH: 1083
<212> TYPE: DNA
```

<213> ORGANISM: Phakopsora pachyrhizi

<400> SEQUENCE: 1

```
atgtctcccc ctgatggttc atccgtgaca gccacggagc ttgcaaaggc tggtgatcta     60
agaaaccgaa aaggtatggc tcagtatacc aacttctgga aaaatgacca gtcaaaagat    120
cccaaggcag acggggagag gagaaaagag cagtaccaag acttggtgaa tggttactat    180
gactgcgtaa ccgaccttta cgagtacggc tggggccaga actttcattt ttgtcgtttt    240
tacaagggtg aagcctttgc ccagggaatt gctcgacatg aacactacct tgcggcgcag    300
atcggaatta aggagaacat gaaggttctc gacgttgggt gtggtgtcgg gggtccggca    360
agagagatct gttggttctc agacgcaaac atcgtcggga tcaacaataa catattccag    420
gtcgaccgtg cgatcaagta tgccgcaaag gccggattgt ctcacaagtt gacgtttgag    480
aaaggtaatt ttatggacat ggccagtcag tttggcgaaa atacctttga tgccgtctat    540
gctatagaag ctactgtcca tgctccaaac tgtgagggag tgtacggaga ggtttttaag    600
gttttaaaac ctggaggtgt ctttggattt tacgagtggt gcttgaccga caagtttaat    660
gaaaatgatg ccgctcatcg acagattcgg catgaaatcg agcttggaga tgcgattcca    720
gagctccgaa ctattgaaag atcggccgag ggcttgaagg ctgtcggatt tgagatcatg    780
aagtctgaag atctggctac caggaaggat ccacttcctt ggtactaccc tctccgtggt    840
agcctttcgg aggctcaaac cttatgggat tatgtcacca tattccgctt gacgactttt    900
ggtaaagcgt tggcctcaac agctgttagg gttatggaaa ccgttggctt agctccaaaa    960
ggatcatctg ctgcagacaa atctctaaat attgcagctt tatctcttgt caaaggagga   1020
gagacaggaa tatttacacc catgcaattg ttcgtctgcc gcaagccctt taataaacta   1080
taa                                                                 1083
```

<210> SEQ ID NO 2
<211> LENGTH: 951
<212> TYPE: DNA
<213> ORGANISM: Phakopsora pachyrhizi

<400> SEQUENCE: 2

```
gaccgccgag gacggcaagt gactgtatac gactcagctg gagcgaattg gagctccacc     60
gcggtggcgg tcgctctaga actagtggat cccccgggct gcaggaattc gatccggcct    120
ttgcggcata cttgatcgca cggtcgacct ggaatatgtt attgttgatc ccgacgatgt    180
ttgcgtctga gaaccaacag atctctcttg ccggaccccc gacaccacac ccaacgtcga    240
gaaccttcat gttctcctta attccgatct gcgccgcaag gtagtgttca tgtcgagcaa    300
ttccctgggc aaaggcttca cccttgtaaa aacgacaaaa atgaaagttc taggtttttt    360
tacaaagcga ttgtaatttg atcgctcagt caatcttctt cacaagagat aatgattttt    420
caaatgattt ttttaacaat gtgtaactca cctggcccca gccgtactcg taaaggtcgg    480
ttacgcagtc atagtaacca ttcaccaagt cttggtactg ctcttttctc ctctccccgt    540
ctgccttggg atcttttgac tggtcatttt tccagaagtt ggtatactga gccatacctt    600
ttcggtttct tagatcacca gcctttgcaa gctccgtggc tgtcacggat gaaccatcag    660
ggggagacat gttttaaaga tgttttaaga cgtatgtata gattgaggac tgtgtacagg    720
gaggatgggt gaggttaggt gacaggcggg attgtggtat cagttgaagt tctctactga    780
ttgtaggatg gatgaggaag aggtagtact ggaattcatg atcattatct gtgtagattg    840
agttggttct caggcagacc gtatggtgat cgaaaagccc aaacattaca acactggttc    900
```

-continued

```
cgacgttgaa ctcttcattt agtttgaaat tgaaagtcac agtcaaaccc a            951


<210> SEQ ID NO 3
<211> LENGTH: 307
<212> TYPE: DNA
<213> ORGANISM: Phakopsora pachyrhizi

<400> SEQUENCE: 3

cctggaatat gttattgttg atcccgacga tgtttgcgtc tgagaaccaa cagatctctc     60

ttgccggacc cccgacacca cacccaacgt cgagaacctt catgttctcc ttaattccga    120

tctgcgccgc aaggtagtgt tcatgtcgag caattccctg ggcaaaggct tcacccttgt    180

aaaaacgaca aaaatgaaag ttctaggttt ttttacaaag cgattgtaat ttgatcgctc    240

agtcaatctt cttcacaaga gataatgatt tttcaaatga ttttttaac aatgtgtaac    300

tcacctg                                                              307


<210> SEQ ID NO 4
<211> LENGTH: 2200
<212> TYPE: DNA
<213> ORGANISM: Artificial Sequence
<220> FEATURE:
<223> OTHER INFORMATION: vector construct useful for RNAi agianst SMT1

<400> SEQUENCE: 4

aattcgaatc caaaaattac ggatatgaat ataggcatat ccgtatccga attatccgtt     60

tgacagctag caacgattgt acaattgctt ctttaaaaaa ggaagaaaga aagaaagaaa    120

agaatcaaca tcagcgttaa caaacggccc cgttacggcc caaacggtca tatagagtaa    180

cggcgttaag cgttgaaaga ctcctatcga aatacgtaac cgcaaacgtg tcatagtcag    240

atcccctctt ccttcaccgc ctcaaacaca aaaataatct tctacagcct atatatacaa    300

cccccccttc tatctctcct ttctcacaat tcatcatctt tctttctcta cccccaattt    360

taagaaatcc tctcttctcc tcttcatttt caaggtaaat ctctctctct ctctctctct    420

ctgttattcc ttgttttaat taggtatgta ttattgctag tttgttaatc tgcttatctt    480

atgtatgcct tatgtgaata tctttatctt gttcatctca tccgtttaga agctataaat    540

ttgttgattt gactgtgtat ctacacgtgg ttatgtttat atctaatcag atatgaattt    600

cttcatattg ttgcgtttgt gtgtaccaat ccgaaatcgt tgattttttt catttaatcg    660

tgtagctaat tgtacgtata catatggatc tacgtatcaa ttgttcatct gtttgtgttt    720

gtatgtatac agatctgaaa acatcacttc tctcatctga ttgtgttgtt acatacatag    780

atatagatct gttatatcat tttttttatt aattgtgtat atatatatgt gcatagatct    840

ggattacatg attgtgatta tttacatgat tttgttattt acgtatgtat atatgtagat    900

ctggactttt tggagttgtt gacttgattg tatttgtgtg tgtatatgtg tgttctgatc    960

ttgatatgtt atgtatgtgc agcccggatc aagggcgaat tcgacccaag tttgtacaaa   1020

aaagcaggct ggcgcgccca ggtgagttac acattgttaa aaaaatcatt tgaaaaatca   1080

ttatctcttg tgaagaagat tgactgagcg atcaaattac aatcgctttg taaaaaaacc   1140

tagaactttc atttttgtcg tttttacaag ggtgaagcct ttgcccaggg aattgctcga   1200

catgaacact accttgcggc gcagatcgga attaaggaga acatgaaggt tctcgacgtt   1260

gggtgtggtg tcgggggtcc ggcaagagag atctgttggt tctcagacgc aaacatcgtc   1320

gggatcaaca ataacatatt ccagggacgt ctaaataact aatactcccc gagtctgaac   1380
```

-continued

```
cgctcgatcg aacctcactc aacactgacg agagcgagtc gtctaactct tgcagcctct   1440

ttgcgtcgtg aaagctctct ggatccccga gaaactcgga taagagactc acagagtagc   1500

caccctcggt cacaacgcta caatcgtcca agctcgtaag ctcgaagccg aagtccagat   1560

ctgtgctggc gaagtcgatc tcggacttaa gaacttcctc caaatcgcgg tcgcagtctt   1620

caaattcgtt agttatttac tcgagaacag atctctcttg ccggaccccc gacaccacac   1680

ccaacgtcga gaaccttcat gttctcctta attccgatct gcgccgcaag gtagtgttca   1740

tgtcgagcaa ttccctgggc aaaggcttca ccccttgtaaa aacgacaaaa atgaaagttc   1800

taggtttttt tacaaagcga ttgtaatttg atcgctcagt caatcttctt cacaagagat   1860

aatgattttt caaatgattt ttttaacaat gtgtaactca cctgcctgca ggggggaccc   1920

agctttcttg tacaaagtgg gacctaggat cgttcaaaca tttggcaata aagtttctta   1980

agattgaatc ctgttgccgg tcttgcgatg attatcatat aatttctgtt gaattacgtt   2040

aagcatgtaa taattaacat gtaatgcatg acgttattta tgagatgggt ttttatgatt   2100

agagtcccgc aattatacat ttaatacgcg atagaaaaca aaatatagcg cgcaaactag   2160

gataaattat cgcgcgcggt gtcatctatg ttactagatc                         2200


<210> SEQ ID NO 5
<211> LENGTH: 360
<212> TYPE: PRT
<213> ORGANISM: Phakopsora pachyrhizi

<400> SEQUENCE: 5

Met Ser Pro Pro Asp Gly Ser Ser Val Thr Ala Thr Glu Leu Ala Lys
1               5                   10                  15

Ala Gly Asp Leu Arg Asn Arg Lys Gly Met Ala Gln Tyr Thr Asn Phe
            20                  25                  30

Trp Lys Asn Asp Gln Ser Lys Asp Pro Lys Ala Asp Gly Glu Arg Arg
        35                  40                  45

Lys Glu Gln Tyr Gln Asp Leu Val Asn Gly Tyr Tyr Asp Cys Val Thr
    50                  55                  60

Asp Leu Tyr Glu Tyr Gly Trp Gly Gln Asn Phe His Phe Cys Arg Phe
65                  70                  75                  80

Tyr Lys Gly Glu Ala Phe Ala Gln Gly Ile Ala Arg His Glu His Tyr
                85                  90                  95

Leu Ala Ala Gln Ile Gly Ile Lys Glu Asn Met Lys Val Leu Asp Val
            100                 105                 110

Gly Cys Gly Val Gly Gly Pro Ala Arg Glu Ile Cys Trp Phe Ser Asp
        115                 120                 125

Ala Asn Ile Val Gly Ile Asn Asn Asn Ile Phe Gln Val Asp Arg Ala
    130                 135                 140

Ile Lys Tyr Ala Ala Lys Ala Gly Leu Ser His Lys Leu Thr Phe Glu
145                 150                 155                 160

Lys Gly Asn Phe Met Asp Met Ala Ser Gln Phe Gly Glu Asn Thr Phe
                165                 170                 175

Asp Ala Val Tyr Ala Ile Glu Ala Thr Val His Ala Pro Asn Cys Glu
            180                 185                 190

Gly Val Tyr Gly Glu Val Phe Lys Val Leu Lys Pro Gly Gly Val Phe
        195                 200                 205

Gly Phe Tyr Glu Trp Cys Leu Thr Asp Lys Phe Asn Glu Asn Asp Ala
    210                 215                 220

Ala His Arg Gln Ile Arg His Glu Ile Glu Leu Gly Asp Ala Ile Pro
```

-continued 225 230 235 240

Glu Leu Arg Thr Ile Glu Arg Ser Ala Glu Gly Leu Lys Ala Val Gly
245 250 255

Phe Glu Ile Met Lys Ser Glu Asp Leu Ala Thr Arg Lys Asp Pro Leu
260 265 270

Pro Trp Tyr Tyr Pro Leu Arg Gly Ser Leu Ser Glu Ala Gln Thr Leu
275 280 285

Trp Asp Tyr Val Thr Ile Phe Arg Leu Thr Thr Phe Gly Lys Ala Leu
290 295 300

Ala Ser Thr Ala Val Arg Val Met Glu Thr Val Gly Leu Ala Pro Lys
305 310 315 320

Gly Ser Ser Ala Ala Asp Lys Ser Leu Asn Ile Ala Ala Leu Ser Leu
325 330 335

Val Lys Gly Gly Glu Thr Gly Ile Phe Thr Pro Met Gln Leu Phe Val
340 345 350

Cys Arg Lys Pro Phe Asn Lys Leu
355 360

<210> SEQ ID NO 6
<211> LENGTH: 982
<212> TYPE: DNA
<213> ORGANISM: Petroselinum crispum
<400> SEQUENCE: 6
aattcgaatc caaaaattac ggatatgaat ataggcatat ccgtatccga attatccgtt 60
tgacagctag caacgattgt acaattgctt ctttaaaaaa ggaagaaaga aagaaagaaa 120
agaatcaaca tcagcgttaa caaacggccc cgttacggcc caaacggtca tatagagtaa 180
cggcgttaag cgttgaaaga ctcctatcga aatacgtaac cgcaaacgtg tcatagtcag 240
atcccctctt ccttcaccgc ctcaaacaca aaaataatct tctacagcct atatatacaa 300
cccccccttc tatctctcct ttctcacaat tcatcatctt tctttctcta cccccaattt 360
taagaaatcc tctcttctcc tcttcatttt caaggtaaat ctctctctct ctctctctct 420
ctgttattcc ttgttttaat taggtatgta ttattgctag tttgttaatc tgcttatctt 480
atgtatgcct tatgtgaata tctttatctt gttcatctca tccgtttaga agctataaat 540
ttgttgattt gactgtgtat ctacacgtgg ttatgtttat atctaatcag atatgaattt 600
cttcatattg ttgcgtttgt gtgtaccaat ccgaaatcgt tgattttttt catttaatcg 660
tgtagctaat tgtacgtata catatggatc tacgtatcaa ttgttcatct gtttgtgttt 720
gtatgtatac agatctgaaa acatcacttc tctcatctga ttgtgttgtt acatacatag 780
atatagatct gttatatcat ttttttatt aattgtgtat atatatatgt gcatagatct 840
ggattacatg attgtgatta tttacatgat tttgttattt acgtatgtat atatgtagat 900
ctggactttt tggagttgtt gacttgattg tatttgtgtg tgtatatgtg tgttctgatc 960
ttgatatgtt atgtatgtgc ag 982

<210> SEQ ID NO 7
<211> LENGTH: 307
<212> TYPE: DNA
<213> ORGANISM: Phakopsora pachyrhizi
<400> SEQUENCE: 7
caggtgagtt acacattgtt aaaaaaatca tttgaaaaat cattatctct tgtgaagaag 60
attgactgag cgatcaaatt acaatcgctt tgtaaaaaaa cctagaactt tcatttttgt 120
cgtttttaca agggtgaagc ctttgcccag ggaattgctc gacatgaaca ctaccttgcg 180
gcgcagatcg gaattaagga gaacatgaag gttctcgacg ttgggtgtgg tgtcgggggt 240
ccggcaagag agatctgttg gttctcagac gcaaacatcg tcgggatcaa caataacata 300
ttccagg 307

<210> SEQ ID NO 8
<211> LENGTH: 266
<212> TYPE: DNA
<213> ORGANISM: Physcomitrella patens

<400> SEQUENCE: 8
tactccccga gtctgaaccg ctcgatcgaa cctcactcaa cactgacgag agcgagtcgt 60
ctaactcttg cagcctcttt gcgtcgtgaa agctctctgg atccccgaga aactcggata 120
agagactcac agagtagcca ccctcggtca caacgctaca atcgtccaag ctcgtaagct 180
cgaagccgaa gtccagatct gtgctggcga agtcgatctc ggacttaaga acttcctcca 240
aatcgcggtc gcagtcttca aattcg 266

<210> SEQ ID NO 9
<211> LENGTH: 260
<212> TYPE: DNA
<213> ORGANISM: Phakopsora pachyrhizi

<400> SEQUENCE: 9
aacagatctc tcttgccgga cccccgacac cacacccaac gtcgagaacc ttcatgttct 60
ccttaattcc gatctgcgcc gcaaggtagt gttcatgtcg agcaattccc tgggcaaagg 120
cttcaccctt gtaaaaacga caaaaatgaa agttctaggt ttttttacaa agcgattgta 180
atttgatcgc tcagtcaatc ttcttcacaa gagataatga tttttcaaat gattttttta 240
acaatgtgta actcacctgc 260

<210> SEQ ID NO 10
<211> LENGTH: 253
<212> TYPE: DNA
<213> ORGANISM: Agrobacterium tumefaciens

<400> SEQUENCE: 10
gatcgttcaa acatttggca ataaagtttc ttaagattga atcctgttgc cggtcttgcg 60
atgattatca tataatttct gttgaattac gttaagcatg taataattaa catgtaatgc 120
atgacgttat ttatgagatg ggtttttatg attagagtcc cgcaattata catttaatac 180
gcgatagaaa acaaaatata gcgcgcaaac taggataaat tatcgcgcgc ggtgtcatct 240
atgttactag atc 253

<210> SEQ ID NO 11
<211> LENGTH: 26
<212> TYPE: DNA
<213> ORGANISM: Artificial Sequence
<220> FEATURE:
<223> OTHER INFORMATION: antisense forward primer

<400> SEQUENCE: 11
ggcgcgccca ggtgagttac acattg 26

<210> SEQ ID NO 12
<211> LENGTH: 26
<212> TYPE: DNA

-continued

```
<213> ORGANISM: Artificial Sequence
<220> FEATURE:
<223> OTHER INFORMATION: antisense reverse primer

<400> SEQUENCE: 12

gacgtccctg gaatatgtta ttgttg                                  26


<210> SEQ ID NO 13
<211> LENGTH: 27
<212> TYPE: DNA
<213> ORGANISM: Artificial Sequence
<220> FEATURE:
<223> OTHER INFORMATION: sense forward primer

<400> SEQUENCE: 13

ctcgagaaca gatctctctt gccggac                                 27


<210> SEQ ID NO 14
<211> LENGTH: 25
<212> TYPE: DNA
<213> ORGANISM: Artificial Sequence
<220> FEATURE:
<223> OTHER INFORMATION: sense reverse primer

<400> SEQUENCE: 14

ctgcaggcag gtgagttaca cattg                                   25
```

METHODS FOR INCREASING THE RESISTANCE OF PLANTS TO FUNGI BY SILENCING THE FUNGAL SMT1-GENE

RELATED APPLICATIONS

This application is a national stage application (under 35 U.S.C. §371) of PCT/EP2010/068951, filed Dec. 6, 2010, which claims benefit of U.S. Provisional Application 61/267,864, filed Dec. 9, 2009, and European Patent Application No. 09178538.6, filed Dec. 9, 2009.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing__13987__00191_US. The size of the text file is 14 KB and the text file was created on Jun. 7, 2012.

The present invention relates to methods for generating or increasing resistance to at least one fungi, in particular soy bean rust, in a plant or a part of a plant by the expression of RNA which is at least partial complementary and/ or partial identical to the STM1-gene, wherein the RNA is capable to provide ds-RNA and/or siRNA and/or miRNA. Moreover, the invention relates to respective plants, parts thereof and vector constructs capable to provide such RNA and the use of such vector constructs to provide fungal resistant plants.

The cultivation of agricultural crop plants serves mainly for the production of foodstuffs for humans and animals. Monocultures in particular, which are the rule nowadays, are highly susceptible to an epidemic-like spreading of diseases. The result is markedly reduced yields. To date, the pathogenic organisms have been controlled mainly by using pesticides. Nowadays, the possibility of directly modifying the genetic disposition of a plant or pathogen is also open to man.

Fungi are distributed worldwide. Approximately 100 000 different fungal species are known to date. The rusts are of great importance. They can have a complicated development cycle with up to five different spore stages (spermatium, aecidiospore, uredospore, teleutospore and basidiospore).

During the infection of plants by pathogenic fungi, different phases are usually observed. The first phases of the interaction between phytopathogenic fungi and their potential host plants are decisive for the colonization of the plant by the fungus. During the first stage of the infection, the spores become attached to the surface of the plants, germinate, and the fungus penetrates the plant. Fungi may penetrate the plant via existing ports such as stomata, lenticels, hydatodes and wounds, or else they penetrate the plant epidermis directly as the result of the mechanical force and with the aid of cell-wall-digesting enzymes. Specific infection structures are developed for penetration of the plant. The soya rust *Phakopsora pachyrhizi* directly penetrates the plant epidermis.

The biotrophic phytopathogenic fungi, such as many rusts, depend for their nutrition on the metabolism of live cells of the plants. The necrotrophic phytopathogenic fungi depend for their nutrition on dead cells of the plants. Soybeanrust has occupied an intermediate position since it penetrates the epidermis directly, whereupon the penetrated cell becomes necrotic. After the penetration, the fungus changes over to an obligatory-biotrophic lifestyle. The subgroup of the biotrophic fungal pathogens which follows essentially such an infection strategy will, for the purposes of the present invention, be referred to as being "hemibiotrophic".

Soybean rust has become increasingly important in recent times. The disease may be caused by the pathogenic rusts Phakopsora pachyrhizi (Sydow) and Phakopsora meibomiae (Arthur). They belong to the class Basidiomycota, order Uredinales, family Phakopsoraceae. Both rusts infect a wide spectrum of leguminosic host plants. *P. pachyrhizi*, also referred to as Asian soybean rust, is the more aggressive pathogen on soybeans (*Glycine max*), and is therefore, at least currently, of great importance for agriculture. *P. pachyrhizi* can be found in nearly all tropical and subtropical soybean growing regions of the world. *P. pachyrhizi* is capable of infecting 31 species from 17 families of the Leguminosae under natural conditions and is capable of growing on further 60 species under controlled conditions (Sinclair et al. (eds.), Proceedings of the soybean rust workshop (1995), National Soybean Research Laboratory, Publication No. 1 (1996); Rytter J. L. et al., Plant Dis. 87, 818 (1984)). *P. meibomiae* has been found in the Caribbean Basin and in Puerto Rico, and has not caused substantial damage as yet.

*P. pachyrhizi* can currently be controlled in the field only by means of fungicides. Soybean plants with resistance to the entire spectrum of the isolates are not available. When searching for resistant plants, four dominant genes Rpp1-4, which mediate resistance of soya to *P. pachyrhizi*, were discovered. The resistance was lost rapidly. Further, all crosses have only led to sterile progeny.

In recent years, fungal diseases, e.g. soybean rust, has gained in importance as pest in agricultural production. There was therefore a demand in the prior art for developing methods to control fungi and to provide fungal resistant plants.

Ergosterol is a component of fungal cell membranes, serving the same function that cholesterol serves in animal cells. Sterol methyltransferase (SMT1) is a key enzyme of the ergosterol biosynthesis pathway. It has been surprisingly found that fungal resistance can be provided by introducing recombinant nucleic acids into plant cells capable of silencing the fungal SMT1-gene in fungi, in particular by RNAi, mi-RNA, sense and/or antisense techniques. A person skilled in the art would not have assumed that indirectly silencing the fungal SMT-1 gene by transformation of the host plant would provide fungal resistance to the plant.

The present invention provides a method for producing a plant and/or a part thereof resistant to a phythopathogenic fungus comprising a) providing a recombinant nucleic acid comprising a target nucleic acid that is substantial identical and/or substantial complementary to at least contiguous 19 nucleotides of the target SMT1-sequence,
b) introducing said recombinant nucleic acid into in the plant and/or parts thereof.

The present invention further provides a vector construct comprising a recombinant nucleic acid comprising a promoter that is functional in the plant cell, operably linked to a target nucleic acid which is substantial identical and/or substantial complementary to at least 19 contiguous nucleotides of the target SMT1-gene and a terminator regulatory sequence as well as the use of the vector construct for the transformation of plants or parts thereof to provide fungal resistant plants.

The present invention also provides a transgenic plant cell, plants or parts thereof comprising a recombinant nucleic acid comprising a target nucleic acid that is substantial identical and/or substantial complementary at least contiguous 19 nucleotides of the target SMT1-gene. Parts of plants may be plant cells, roots, stems, leaves, flowers and/or seeds.

Without to be bound by this theory it is assumed that the plant is producing small interfering (si)RNAs from the SMT1 construct by using the pathways known in the literature (Andrew Eamens, Ming-Bo Wang, Neil A. Smith, and Peter M. Waterhouse "RNA Silencing in Plants: Yesterday, Today, and Tomorrow" Plant Physiology, June 2008, Vol. 147, pp. 456-468). Due to the close connection between the fungus and its host plant (especially at the haustoria), the siRNAs are able to move or being transported (in complexes with proteins or naked) into the fugus. In the fungus the siRNAs lead to a sequence specific siRNA mediated knock-down of the target gene (in this case SMT1). This process is most likely mediated and maintained by protein complexes like RISC (RNA-induced silencing complex) and RdRP (RNA dependent RNA polymerases).

The present invention may be understood more readily by reference to the following detailed description of the preferred embodiments of the invention and the examples included herein. Unless otherwise noted, the terms used herein are to be understood according to conventional usage by those of ordinary skill in the relevant art. In addition to the definitions of terms provided herein, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement). It is to be understood that as used in the specification and in the claims, "a" or "an" can mean one or more, depending upon the context in which it is used. Thus, for example, reference to "a cell" can mean that at least one cell can be utilized. It is to be understood that the terminology used herein is for the purpose of describing specific embodiments only and is not intended to be limiting.

Throughout this application, various publications are referenced. The disclosures of all of these publications and those references cited within those publications in their entireties are hereby incorporated by reference into this application in order to more fully describe the state of the art to which this invention pertains. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth Enzymol. 68;

Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

As used herein the terms "fungal-resistance, resistant to a fungus" and/or "fungal-resistant" mean reducing or preventing an infection by a fungus. Resistance does not imply that the plant necessarily has 100% resistance to infection. In preferred embodiments, the resistance to infection by a fungus in a resistant plant is greater than 10%, 20%, 30%, 40%, 50%, 60%, 70%, 80%, 90%, or 95% in comparison to a wild type plant that is not resistant to fungus. Preferably the wild type plant is a plant of a similar, more preferably identical, genotype as the plant having increased resistance to the fungus, but does not comprise a recombinant nucleic acid comprising the target nucleic acid that is substantial identical and/or complementary to at least 19 nucleotides of the target SMT1-gene. The terms terms "fungal-resistance, "resistant to a fungus" and/or "fungal-resistant" as used herein refers to the ability of a plant, as compared to a wild type plant, to avoid infection by fungus, to kill fungus, to hamper, reduce, to stop the development, growth and/or multiplication of fungus. The level of fungal resistance of a plant can be determined in various ways, e.g. by scoring/measuring the infected leaf area in relation to the overall leaf area. Another possibility to determine the level of resistance is to count the number of fungal colonies on the plant or to measure the amount of spores produced by these colonies. Another way to resolve the degree of fungal infestation is to specifically measure the amount of fungal DNA by quantitative (q) PCR. Specific probes and primer sequences for most fungal pathogens are available in the literature (Frederick R D, Snyder C L, Peterson G L, et al. 2002 Polymerase chain reaction assays for the detection and discrimination of the soybean rust pathogens *Phakopsora pachyrhizi* and *P-meibomiae* PHYTOPATHOLOGY 92(2) 217-227).

As used herein the term "recombinant nucleic acid" refers to a DNA-molecule comprising a nucleic acid that is substantial identical and/or substantial complementary to at least 19 contiguous nucleotides of the fungal SMT1-gene, optionally operably linked to a promoter functional in a plant cell and/or other regulatory sequences. Preferably, the recombinant nucleic acid comprises a sequence which does not naturally occur in the wildtype plant. More preferably, the recombinant nucleic acid comprises a sequence which does occur in fungi but not in plants.

As used herein the term "target nucleic acid" preferably refers to a DNA-molecule capable to prevent the expression, reduce the amount and/or function of the fungal SMT1-protein in the plant, parts of the plant, fungus and/or parts of the fungus.

Generally, the term "substantially identical" preferably refers to DNA and/or RNA which is at least 80% identical to 19 or more contiguous nucleotides of a specific DNA or RNA sequence of the SMT1-gen, more preferably, at least 90% identical to 19 or more contiguous nucleotides, and most preferably at least 95%, at least 96%, at least 97%, at least 98% or at least 99% identical or absolutely identical to 19 or more contiguous nucleotides of a specific DNA or RNA-sequence of the SMT1-gen. In particular the RNA corresponds to the coding DNA-strand of the SMT1-gen.

As used herein, the term "substantially identical" as applied to DNA of the recombinant nucleic acid, the target nucleic acid and/or the target SMT1-gene means that the nucleotide sequence is at least 80% identical to 19 or more contiguous nucleotides of the target SMT1-gene, more preferably, at least 90% identical to 19 or more contiguous nucleotides of the target SMT1-gene, and most preferably at least 95%, at least 96%, at least 97%, at least 98% or at least 99% identical or absolutely identical to 19 or more contiguous nucleotides of the target SMT1-gene. The term "19 or more contiguous nucleotides of the target SMT1-gene" corresponds to the target SMT1-gene, being at least about 19, 20, 21, 22, 23, 24, 25, 50, 100, 200, 300, 400, 500, 1000, 1500, consecutive bases or up to the full length of the target SMT1-gene.

As used herein, "complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other. As used herein, the term "substantially complementary" means that two nucleic acid sequences are complementary over at least at 80% of their nucleotides. Preferably, the two nucleic acid sequences are complementary over at least at 85%, at least 90%, at least 95%, at least 96%, at least 97%, at least 98%, at least 99% or more or all of their nucleotides. Preferably, the two nucleic acid sequences are complementary at least about 19, 20, 21, 22, 23, 24, 25, 50, 100, 200, 300, 400, 500, 1000, 1500, consecutive bases or up to the full length of the target SMT1-gene. Alternatively, "substantially complementary" means that two nucleic acid sequences can hybridize under stringency conditions.

Hybridization: The term "hybridization" as used herein includes "any process by which a strand of nucleic acid molecule joins with a complementary strand through base pairing." (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules. As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: Tm=81.5+0.41(% G+C), when a nucleic acid molecule is in aqueous solution at 1 M NaCl [see e.g., Anderson and Young, Quantitative Filter Hybridization, in Nucleic Acid Hybridization (1985)]. Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

In particular, the term stringency conditions refers to conditions, wherein 100 contigous nucleotides or more, 150 contigous nucleotides or more, 200 contigous nucleotides or more or 250 contigous nucleotides or more which are a fragment or identical to the complementary nucleic acid molecule (DNA, RNA, ssDNA orssRNA) hybridizes under conditions equivalent to hybridization in 7% sodium dodecyl sulfate (SDS), 0.5 M NaPO4, 1 mM EDTA at 50° C. with washing in 2× SSC, 0.1% SDS at 50° C. or 65° C., preferably 65° C. with a specific nucleic acid molecule (DNA; RNA, ssDNA or ss RNA). Preferably, the hybridizing conditions are equivalent to hybridization in 7% sodium dodecyl sulfate (SDS), 0.5 M NaPO4, 1 mM EDTA at 50° C. with washing in 1× SSC, 0.1% SDS at 50° C. or 65° C., preferably 65° C., more preferably the hybridizing conditions are equivalent to hybridization in 7% sodium dodecyl sulfate (SDS), 0.5 M NaPO4, 1 mM EDTA at 50° C. with washing in 0.1× SSC, 0.1% SDS at 50° C. or 65° C., preferably 65° C. Preferably, the complementary nucleotides hybridize with a fragment or the whole SMT1-target gene. Preferably, the complementary polynucleotide hybridizes with parts of the SMT1-target gene capable to provide fungal resistance. In particular, the complementary polynucleotide hybridizes with the coding strand of the SMT1-gene or a part thereof.

As used herein a RNA complementary to a DNA means that the sequence of the RNA is complementary to the coding strand of the DNA.

Preferably two complementary RNAs are reverse complementary to each other, i.e. form dsRNA.

As used herein, the term "target SMT1-gene" means fungal steroyl-methyl-transferase-genes including any homolog of the sterol methyl transferase. In particular, the term SMT1-gene refers to a gene having at least 60% identity with SEQ-ID-No. 1, SEQ-ID-No. 2 or SEQ-ID-No. 3 or with a sequence coding for a protein having SEQ-ID-No. 5. In one embodiment homologues of the SMT1-gene have, at the DNA level or protein level, at least 70%, preferably of at least 80%, especially preferably of at least 90%, quite especially preferably of at least 95%, quite especially preferably of at least 98% or 100% identity over the entire DNA region or protein region given in a sequence specifically disclosed herein.

"Identity" or "complementarity" between two nucleic acids refers preferably in each case over the entire length of the nucleic acid.

For example the identity may be calculated by means of the Vector NTI Suite 7.1 program of the company Informax (USA) employing the Clustal Method (Higgins D G, Sharp P M. Fast and sensitive multiple sequence alignments on a microcomputer. Comput Appl. Biosci. 1989 Apr; 5(2):151-1) with the following settings:

Multiple alignment parameter:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise alignment parameter:

| | |
|---|---|
| FAST algorithm | on |
| K-tuple size | 1 |
| Gap penalty | 3 |
| Window size | 5 |
| Number of best diagonals | 5 |

Alternatively the identity may be determined according to Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, the web page: http://www.ebi.ac.uk/Tools/clustalw/index.html# and the following settings

| | |
|---|---|
| DNA Gap Open Penalty | 15.0 |
| DNA Gap Extension Penalty | 6.66 |
| DNA Matrix | Identity |

-continued

| | |
|---|---|
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

The complementarity may be calculated as the identity. However, complementary means that purines will base pair with pyrimidines to form a combination of guanine paired with cytosine (G:C) and adenine paired with either thymine (A:T) in the case of DNA, or adenine paired with uracil (A:U) in the case of RNA.

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

There is general agreement that in many organisms, including fungi and plants, large pieces of dsRNA complementary to a specific genes are cleaved into 19-24 nucleotide fragments (siRNA) within cells, and that these siRNAs are the actual mediators for silencing the specific target gene. As used herein siRNA refers to 19-24 nucleotide fragments complementary to the target SMT1-gen.

There are several possibilities to provide the si-RNA: RNA-interference (RNAi), micro-RNAi (mi-RNA), sense RNA and/or antisense RNA.

As used herein, "RNAi" or "RNA interference" refers to the process of sequence-specific post-transcriptional gene silencing, mediated by double-stranded RNA (dsRNA). In the RNAi process, dsRNA comprising a first strand that is substantially complementary to at least 19 contiguous nucleotides of the target SMT1-gene and a second strand that is complementary to the first strand at least partially has to be provided. For this purpose a recombinant nucleic acid is introduced into the plant, which is capable to produce such dsRNA. The target SMT1-gene-specific dsRNA is produced and processed into relatively small fragments (siRNAs) and can subsequently become distributed from the plant to the fungus. miRNA refers to a similar process, except that the produced dsRNA only partially comprises regions substantially identical to the SMT1-gene (at least 19 contiguous nucleotides).

As used herein, "antisense interference" refers to the process of sequence-specific post-transcriptional gene silencing, probably also mediated by double-stranded RNA (dsRNA). In the antisense RNA-process, ssRNA comprising a first strand that is substantially complementary to at least 19 contiguous nucleotides of the target SMT1-gene has to be provided. For this purpose recombinant nucleic acid is introduced into the plant, which is capable to produce such ssRNA. Without to be bound by the theory, it is assumed that this RNA moves from the plant to the fungus and subsequently pairs with complementary ssRNA transcribed from the original SMT1-gene produced by the original SMT1-gene. The resulting dsRNA is processed into relatively small fragments (siRNAs) and can subsequently become distributed from the plant to the fungus.

As disclosed herein, 100% sequence identity between the target nucleic acid and the target gene is not required to practice the present invention. Preferably, the target nucleic acid comprises a 19-nucleotide portion which is substantially identical and/or substantially complementary to at least 19 contiguous nucleotides of the target SMT1-gene. While a target nucleic acid comprising a nucleotide sequence identical and/or identical to a portion of the fungal target SMT1-gene and/or complementary to the whole sequence and/or a portion of the fungal target SMT1-gene is preferred for inhibition, the invention can tolerate sequence variations that might be expected due to gene manipulation or synthesis, genetic mutation, strain polymorphism, or evolutionary divergence. Thus the target nucleic acid may also encompass a mismatch with the target SMT1-gene of at least 1, 2, or more nucleotides. For example, it is contemplated in the present invention that within 21 contiguous nucleotides the target nucleic acid may contain an addition, deletion or substitution of 1, 2, or more nucleotides, so long as the resulting RNA sequence still interferes with the fungal target SMT1-gene function.

Sequence identity between the recombinant nucleic acid useful according to the present invention and the fungal SMT1-target gene may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 80% sequence identity, 90% sequence identity, or even 100% sequence identity, between the target nucleic acid and at least 19 contiguous nucleotides of the target gene is preferred. The same preferably applies for the sequence complementarity.

When the target nucleic acid of the invention has a length longer than about 19 nucleotides, for example from about 50 nucleotides to about 500 nucleotides, the corresponding ds RNA provided therefrom will be cleaved randomly to dsRNAs of about 21 nucleotides within the plant or fungal cell: the siRNAs. Multiple specialized Dicers in plants may generate siRNAs typically ranging in size from 19 nt to 24 nt (See Henderson et al., 2006. Nature Genetics 38:721-725.). The cleavage of a longer dsRNA of the invention may yield a pool of 21 mer dsRNAs, derived from the longer dsRNA. The siRNAs may have sequences corresponding to fragments of 19-24 contiguous nucleotides across the entire sequence of the fungal target SMT1-gene. One of skill in the art would recognize that the siRNA can have a mismatch with the target gene of at least 1, 2, or more nucleotides. Further, these mismatches are intended to be included in the present invention.

In one embodiment the target nucleic acid is substantial identical and/or substantial complementary over a length of at least 19, at least 50, at least 100, at least 200, at least 300, at least 400 or at least 500 nucleotides to the target SMT1-gene. In particular, the target nucleic acid may comprise 19 to 500, preferably 50 to 500, more preferably 250 to 350 nucleotides, wherein preferably at least about 19, 20, 21, 22, 23, 24, 25, 50, 100, 200, 300, 400, consecutive bases or up to the full length of target nucleic acid are identical and/or complementary and/or identical to the target SMT1-gene.

Preferably, the recombinant nucleic acid is able to provide dsRNA and/or siRNA and/or miRNA in the plant, a part thereof and/or the fungus infecting the plant or a part thereof once the recombinant nucleic acid is expressed in the plant, wherein preferably at least 19 contiguous nucleotides of the dsRNA and/or si RNA and/or miRNA are substantially complementary to the target SMT1-gene.

One embodiment according to the present invention, provides a method for producing a plant and/or a part thereof resistant to a fungus, wherein the recombinant nucleic acid comprises a promoter that is functional in the plant cell, operably linked to a target nucleic acid which is substantial identical and/or substantial complementary to at least 19 contiguous nucleotides of the target SMT1-gene and which, when it is transcribed, generates RNA comprising a first strand having a sequence substantially complementary to at least 19 contiguous nucleotides of the target SMT1-gene and a second strand having a sequence at substantially complementary to the first strand and/or parts thereof, and a terminator regulatory sequence.

The first strand and the second strand may at least partially form dsRNA.

This technique is also refered to as RNAi. In another embodiment the target nucleic acid comprises 19 to 24 contiguous nucleotides of the target sequence which are substantially identical and/or substantially complementary to the target SMT1-gene and the remaining nucleotides of the target nucleic acid are not identical and/or not complementary to the target SMT1-gene. Not-identical means an identity which is lower than 95%, lower that 90%, lower than 80%, lower than 70%, lower than 60% over the whole sequence of the target nucleic acid. Not-complementary means an complementarity which is lower than 95%, lower that 90%, lower than 80%, lower than 70%, lower than 60% over the whole sequence of the target nucleic acid. This technique is also refered to as miRNA.

One embodiment according to the present invention, provides a method for producing a plant and/or a part thereof resistant to a fungus, wherein the recombinant nucleic acid comprises a promoter that is functional in the plant cell, operably linked to a target nucleic acid which, when it is transcribed, generates RNA comprising a first strand having a sequence substantially complementary to at least contiguous 19 nucleotides of the target SMT1-gene, and a terminator regulatory sequence.

Preferably, the first strand generated in the plant forms dsRNA together with a second RNA-strand generated in the fungus which is complementary to the first strand. This technique is also refered to as antisense RNA.

One embodiment according to the present invention, provides a method for producing a plant and/or a part thereof resistant to a fungus, wherein the recombinant nucleic acid comprises a promoter that is functional in the plant cell, operably linked to a target nucleic acid which, when it is transcribed, generates RNA comprising a first strand having a sequence substantially identical to at least contiguous 19 nucleotides of the target SMT1-gene, and a terminator regulatory sequence.

Preferably, the first strand generated in the plant forms dsRNA together with a second RNA-strand generated in the fungus which is complementary to the first strand. This technique is also refered to as sense RNA.

The dsRNA of the invention may optionally comprise a single stranded overhang at either or both ends. Preferably, the single stranded overhang comprises at least two nucleotides at the 3' end of each strand of the dsRNA molecule. The double-stranded structure may be formed by a single self-complementary RNA strand (i.e. forming a hairpin loop) or two complementary RNA strands. RNA duplex formation may be initiated either inside the plant or inside the fungus. When the dsRNA of the invention forms a hairpin loop, it may optionally comprise an intron, as set forth in US 2003/0180945A1 or a nucleotide spacer, which is a stretch of sequence between the complementary RNA strands to stabilize the hairpin transgene in cells. Methods for making various dsRNA molecules are set forth, for example, in WO 99/53050 and in U.S. Pat. No. 6,506,559.

The term "plant" is intended to encompass plants at any stage of maturity or development, as well as any tissues or organs (plant parts) taken or derived from any such plant unless otherwise clearly indicated by context. Plant parts include, but are not limited to, plant cells, stems, roots, flowers, ovules, stamens, seeds, leaves, embryos, meristematic regions, callus tissue, anther cultures, gametophytes, sporophytes, pollen, microspores, protoplasts, hairy root cultures, and/or the like. The present invention also includes seeds produced by the plants of the present invention. In one embodiment, the seeds are true breeding for an increased resistance to fungal infection as compared to a wild-type variety of the plant seed. As used herein, a "plant cell" includes, but is not limited to, a protoplast, gamete producing cell, and a cell that regenerates into a whole plant. Tissue culture of various tissues of plants and regeneration of plants therefrom is well known in the art and is widely published.

As used herein, the term "transgenic" refers to any plant, plant cell, callus, plant tissue, or plant part that contains all or part of at least one recombinant polynucleotide comprising at least 19 contiguous nucleotides which are substantial identical and/or substantial complementary to the SMT1-gene. Preferably, all or part of the recombinant polynucleotide is stably integrated into a chromosome or stable extra-chromosomal element, so that it is passed on to successive generations.

In one embodiment of the present invention the plant is selected from the group consisting of beans, soya, pea, clover, kudzu, lucerne, lentils, lupins, vetches, and/or groundnut. Preferably the plant is a legume, comprising plants of the genus *Phaseolus* (comprising French bean, dwarf bean, climbing bean (*Phaseolus vulgaris*), Lima bean (*Phaseolus lunatus* L.), Tepary bean (*Phaseolus acutifolius* A. Gray), runner bean (*Phaseolus coccineus*)); the genus *Glycine* (comprising *Glycine soja*, soybeans (*Glycine max* (L.) Merill)); pea (*Pisum*) (comprising shelling peas (*Pisum sativum* L. convar. *sativum*), also called smooth or round-seeded peas; marrowfat pea (*Pisum sativum* L. convar. *medullare* Alef. emend. C.O. Lehm), sugar pea (*Pisum sativum* L. convar. *axiphium* Alef emend. C.O. Lehm), also called snow pea, edible-podded pea or mangetout, (*Pisum granda sneida* L. convar. *sneidulo* p. *shneiderium*)); peanut (*Arachis hypogaea*), clover (*Trifolium* spec.), medick (*Medicago*), kudzu vine (*Pueraria lobata*), common lucerne, alfalfa (*M. sativa* L.), chickpea (*Cicer*), lentils (*Lens*) (*Lens culinaris* Medik.), lupins (*Lupinus*); vetches (*Vicia*), field bean, broad bean (*Vicia faba*), vetchling (*Lathyrus*) (comprising chickling pea (*Lathyrus sativus*), heath pea (*Lathyrus tuberosus*)); genus *Vigna* (comprising moth bean (*Vigna aconitifolia* (Jacq.) Maréchal), adzuki bean (*Vigna angularis* (Willd.) Ohwi & H. Ohashi), urd bean (*Vigna mungo* (L.) Hepper), mung bean (*Vigna radiata* (L.) R. Wilczek), bambara groundnut (*Vigna subterrane* (L.) Verdc.), rice bean (*Vigna umbellata* (Thunb.) Ohwi & H. Ohashi), *Vigna vexillata* (L.) A. Rich., *Vigna unguiculata* (L.) Walp., in the three subspecies asparagus bean, cowpea, catjang bean)); pigeonpea (*Cajanus cajan* (L.) Millsp.), the genus *Macrotyloma* (comprising geocarpa groundnut (*Macrotyloma geocarpum* (Harms) Maréchal & Baudet), horse bean (*Macrotyloma uniflorum* (Lam.) Verdc.)); goa bean (*Psophocarpus tetragonolobus* (L.) DC.), African yam bean (*Sphenostylis stenocarpa* (Hochst. ex A. Rich.) Harms), Egyptian black bean, dolichos bean, lablab bean (*Lablab purpureus* (L.) Sweet), yam bean (*Pachyrhizus*), guar bean (*Cyamopsis tetragonolobus* (L.) Taub.); and/or the genus *Canavalia* (comprising jack bean (*Canavalia ensiformis* (L.) DC.), sword bean (*Canavalia gladiata* (Jacq.) DC.)).

In one embodiment according to the present invention the fungal resistance is a resistance against a biotrophic fungus, preferably a hemibiotrophic fungus. In preferred embodiments of the present invention, the biotrophic fungus is selected from the group Basidiomycota, preferably the Uredinales (rusts), especially preferably the Melompsoraceae, and in particular the genus *Phakopsora*. In especially preferred embodiments, the pathogen is *Phakopsora pachyrhizi* and/or *P. meibomiae* (together also referred to as "soybean rust" or "soya rust"). Preference is being given to the former. When the pathogen is selected from the group of the biotrophic pathogens or fungi, it is preferred in some embodiments that the pathogen is other than powdery mildew or downy mildew.

Further, the present invention provides a vector construct comprising a promoter that is functional in the plant cell, operably linked to a target nucleic acid which is substantially identical and/or substantially complementary to at least 19 contiguous nucleotides of the target SMT1-gene and a terminator regulatory sequence. The expression vector may be isolated.

In one embodiment the vector construct comprises a promoter that is functional in the plant cell, operably linked to a target nucleic acid which is substantial identical and/or substantial complementary to at least 19 contiguous nucleotides of the target SMT1-gene and which, when it is transcribed, generates RNA comprising a first strand having a sequence substantially complementary to at least 19 contiguous nucleotides of the target SMT1-gene and a second strand having a sequence at substantially complementary to the first strand or parts thereof, and a terminator regulatory sequence.

It is preferred that first strand and the second strand are capable of hybridizing to form dsRNA at least partially.

In another embodiment the vector construct comprises a promoter that is functional in the plant cell, operably linked to a target nucleic acid which, when it is transcribed, generates RNA comprising a first strand having a sequence substantially complementary or identical to at least 19 contiguous nucleotides of the target SMT1-gene, and a terminator regulatory sequence.

It is preferred that the transcript of the first strand and at least a part of the transcript of the fungal SMT1-gene are capable of hybridizing to form dsRNA at least partially.

In one embodiment the vector construct comprises a target nucleic acid comprising 19 to 500 nucleotides. Further variants of the target nucleic acid are defined in the section referring to the method for producing a plant.

With respect to a vector construct and/or the recombinant nucleic acid, the term "operatively linked" is intended to mean that the target nucleic acid is linked to the regulatory sequence, including promotors, terminator regulatory sequences, enhancers and/or other expression control elements (e.g., polyadenylation signals), in a manner which allows for expression of the target nucleic acid (e.g., in a host plant cell when the vector is introduced into the host plant cell). Such regulatory sequences are described, for example, in Goeddel, Gene Expression Technology: Methods in Enzymology 185, Academic Press, San Diego, Calif. (1990) and Gruber and Crosby, in: Methods in Plant Molecular Biology and Biotechnology, Eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the vector can depend on such factors as the choice of the host cell to be transformed, the level of expression of dsRNA desired, and the like. The vector constructs of the invention can be introduced into plant host cells to thereby produce ssRNA, dsRNA, siRNA and/or mi RNA in order to prevent and/or reduce fungal infections.

In one embodiment, the vector construct comprises a promotor operatively linked to a target nucleotide that is a template for one or both strands of the ssRNA- or dsRNA molecules at least substantial complementary to 19 contiguous nucleotides of the target SMT1-gen.

In one embodiment, the nucleic acid molecule further comprises two promoters flanking either end of the nucleic acid molecule, wherein the promoters drive expression of each individual DNA strand, thereby generating two complementary RNAs that hybridize and form the dsRNA.

In alternative embodiments, the nucleotide sequence is transcribed into both strands of the dsRNA on one transcription unit, wherein the sense strand is transcribed from the 5' end of the transcription unit and the antisense strand is transcribed from the 3' end, wherein the two strands are separated by about 3 to about 500 base pairs, and wherein after transcription, the RNA transcript folds on itself to form a hairpin.

In another embodiment, the vector contains a bidirectional promoter, driving expression of two nucleic acid molecules, whereby one nucleic acid molecule codes for the sequence substantially identical to a portion of SMT1-gene gene and the other nucleic acid molecule codes for a second sequence being substantially complementary to the first strand and capable of forming a dsRNA, when both sequences are transcribed. A bidirectional promoter is a promoter capable of mediating expression in two directions.

In another embodiment, the vector contains two promoters, one mediating transcription of the sequence substantially identical to a portion of a SMT1 gene and another promoter mediating transcription of a second sequence being substantially complementary to the first strand and capable of forming a dsRNA, when both sequences are transcribed. The second promoter might be a different promoter.

A different promoter means a promoter having a different activity in regard to cell or tissue specificity, or showing expression on different inducers for example, pathogens, abiotic stress or chemicals.

Promoters according to the present invention may be constitutive, inducible, in particular pathogen-induceable, developmental stage-preferred, cell type-preferred, tissue-preferred or organ-preferred. Constitutive promoters are active under most conditions. Non-limiting examples of constitutive promoters include the CaMV 19S and 35S promoters (Odell et al., 1985, Nature 313:810-812), the sX CaMV 35S promoter (Kay et al., 1987, Science 236:1299-1302), the Sep1 promoter, the rice actin promoter (McElroy et al., 1990, Plant Cell 2:163-171), the Arabidopsis actin promoter, the ubiquitin promoter (Christensen et al., 1989, Plant Molec. Biol. 18:675-689); pEmu (Last et al., 1991, Theor. Appl. Genet. 81:581-588), the figwort mosaic virus 35S promoter, the Smas promoter (Velten et al., 1984, EMBO J. 3:2723-2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) promoter, and/or the like. Promoters that express the dsRNA in a cell that is contacted by fungus are preferred. Alternatively, the promoter may drive expression of the dsRNA in a plant tissue remote from the site of contact with the fungus, and the dsRNA may then be transported by the plant to a cell that is contacted by the fungus, in particular cells of, or close by fungal infected sites.

Preferably, the expression vector of the invention comprises a constitutive promoter, root-specific promoter, a pathogen inducible promoter, or a fungal-inducible promoter. A promoter is inducible, if its activity, measured on the amount of RNA produced under control of the promoter, is at least 30%, 40%, 50% preferably at least 60%, 70%, 80%, 90% more preferred at least 100%, 200%, 300% higher in its induced state, than in its un-induced state. A promoter is cell-, tissue- or organ-specific, if its activity , measured on the amount of RNA produced under control of the promoter, is at least 30%, 40%, 50% preferably at least 60%, 70%, 80%, 90% more preferred at least 100%, 200%, 300% higher in a particular cell-type, tissue or organ, then in other cell-types or tissues of the same plant, preferably the other cell-types or tissues are cell types or tissues of the same plant organ, e.g. a root. In the case of organ specific promoters, the promoter activity has to be compared to the promoter activity in other plant organs, e.g. leaves, stems, flowers or seeds.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, leaf-preferred, stigma-preferred, pollen-preferred, anther-preferred, a petal-preferred, sepal-preferred, pedicel-preferred, silique-preferred, stem-preferred, root-preferred promoters and/or the like. Seed preferred promoters are preferentially expressed during seed development and/or germination. For example, seed preferred promoters can be embryo-preferred, endosperm preferred and seed coat-preferred. See Thompson et al., 1989, BioEssays 10:108. Examples of seed preferred promoters include, but are not limited to cellulose synthase (celA), Cim1, gamma-zein, globulin-1, maize 19 kD zein (cZ19B1) and/or the like.

Other suitable tissue-preferred or organ-preferred promoters include, but are not limited to, the napin-gene promoter from rapeseed (U.S. Pat. No. 5,608,152), the USP-promoter from *Vicia faba* (Baeumlein et al., 1991, Mol Gen Genet. 225(3):459-67), the oleosin-promoter from *Arabidopsis* (PCT Application No. WO 98/45461), the phaseolin-promoter from *Phaseolus vulgaris* (U.S. Pat. No. 5,504,200), the Bce4-promoter from Brassica (PCT Application No. WO 91/13980), or the legumin B4 promoter (LeB4; Baeumlein et al., 1992, Plant Journal, 2(2):233-9), as well as promoters conferring seed specific expression in monocot plants like maize, barley, wheat, rye, rice, etc. Suitable promoters to note are the Ipt2 or Ipt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene, and/or rye secalin gene) Promoters useful according to the invention include, but are not limited to, are the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2, bronze promoters, the Zm13 promoter (U.S. Pat. No. 5,086, 169), the maize polygalacturonase promoters (PG) (U.S. Pat. Nos. 5,412,085 and 5,545,546), the SGB6 promoter (U.S. Pat. No. 5,470,359), as well as synthetic or other natural promoters.

Epidermisspezific promotors may be selected from the group consisting of:

WIR5 (=GstA1); acc. X56012; Dudler & Schweizer,

GLP4, acc. AJ310534; Wei Y., Zhang Z., Andersen C. H., Schmelzer E., Gregersen P. L., Collinge D. B., Smedegaard-Petersen V. and Thordal-Christensen H., Plant Molecular Biology 36, 101 (1998), GLP2a, acc. AJ237942, Schweizer P., Christoffel A. and Dudler R., Plant J. 20, 541 (1999);

Prx7, acc. AJ003141, Kristensen B. K., Ammitzböll H., Rasmussen S. K. and Nielsen K. A., Molecular Plant Pathology, 2(6), 311 (2001);

GerA, acc. AF250933; Wu S., Druka A., Horvath H., Kleinhofs A., Kannangara G. and von Wettstein D., Plant Phys Biochem 38, 685 (2000);

OsROC1, acc. AP004656

RTBV, acc. AAV62708, AAV62707; Klöti A., Henrich C., Bieri S., He X., Chen G., Burkhardt P. K., Wünn J., Lucca P., Hohn T., Potrykus I. and Fütterer J., PMB 40, 249 (1999);

Chitinase ChtC2-Promotor from potato (Ancillo et al., Planta. 217(4), 566, (2003));

AtProT3 Promotor (Grallath et al., Plant Physiology. 137 (1), 117 (2005));

SHN-Promotors from Arabidopsis (AP2/EREBP transcription factors involved in cutin and wax production) (Aarón et al., Plant Cell. 16(9), 2463 (2004)); and/or GSTA1 from wheat (Dudler et al., WP2005306368 and Altpeter et al., Plant Molecular Biology. 57(2), 271 (2005)).

Mesophyllspezific promotors may be seleted from the group consisting of:

PPCZm1 (=PEPC); Kausch A. P., Owen T. P., Zachwieja S. J., Flynn A. R. and Sheen J., Plant Mol. Biol. 45, 1 (2001);

OsrbcS, Kyozuka et al., PlaNT Phys 102, 991 (1993); Kyozuka J., McElroy D., Hayakawa T., Xie Y., Wu R. and Shimamoto K., Plant Phys. 102, 991 (1993);

OsPPDK, acc. AC099041;

TaGF-2.8, acc. M63223; Schweizer P., Christoffel A. and Dudler R., Plant J. 20, 541 (1999);

TaFBPase, acc. X53957;

TaWIS1, acc. AF467542; US 200220115849;

HvBIS1, acc. AF467539; US 200220115849;

ZmMIS1, acc. AF467514; US 200220115849;

HvPR1a, acc. X74939; Bryngelsson et al., Mol. Plant Microbe Interacti. 7 (2), 267 (1994);

HvPR1b, acc. X74940; Bryngelsson et al., Mol. Plant Microbe Interact. 7(2), 267 (1994);

HvB1,3gluc; acc. AF479647;

HvPrx8, acc. AJ276227; Kristensen et al., Molecular Plant Pathology, 2(6), 311 (2001); and/or HvPAL, acc. X97313; Wei Y., Zhang Z., Andersen C. H., Schmelzer E., Gregersen P. L., Collinge D. B., Smedegaard-Petersen V. and Thordal-Christensen H. Plant Molecular Biology 36, 101 (1998).

Constitutve promotors may be selected from the group consisting of

PcUbi promoter from parsley (WO 03/102198)

CaMV 35S promoter: Cauliflower Mosaic Virus 35S promoter (Benfey et al. 1989 EMBO J. 8(8): 2195-2202), STPT promoter: *Arabidopsis thaliana* Short Triose phosphat translocator promoter (Accession NM_123979)

Act1 promoter: —Oryza sativa actin 1 gene promoter (McElroy et al. 1990 PLANT CELL 2(2) 163-171a) and/or EF1A2 promoter: Glycine max translation elongation factor EF1 alpha (US 20090133159).

One type of vector construct is a "plasmid," which refers to a circular double stranded DNA loop into which additional DNA segments can be ligated. Another type of vector is a viral vector, wherein additional DNA segments can be ligated into the viral genome. Certain vector constructs are capable of autonomous replication in a host plant cell into which they are introduced. Other vector constructs are integrated into the genome of a host plant cell upon introduction into the host cell, and thereby are replicated along with the host genome. In particular the vector construct is capable of directing the expression of gene to which the vectors is operatively linked. However, the invention is intended to include such other forms of expression vector constructs, such as viral vectors (e.g., potato virus X, tobacco rattle virus, and/or Gemini virus), which serve equivalent functions.

A preferred vector construct comprises sequences selected from the group consisting of SEQ-ID-1, 2, 3, 4, 6, 7, 8, 9 and/or 10.

The present invention further provides a transgenic plant cell comprising a recombinant nucleic acid comprising a target nucleic acid that is substantial identical and/or substantially complementary to at least contiguous 19 nucleotides of the target SMT1-gene. The present invention further provides a transgenic plant or parts thereof comprising the above transgenic plant cells according or consisting thereof. The present invention also provides transgenic seeds derived from the plant comprising the target nucleic acid. Parts of the plant may be root, leaves and/or flowers.

The transgenic plant cells may be transformed with one of the above described vector constructs. Suitable methods for transforming or transfecting host cells including plant cells are well known in the art of plant biotechnology. Any method may be used to transform the recombinant expression vector into plant cells to yield the transgenic plants of the invention. General methods for transforming dicotyledenous plants are disclosed, for example, in U.S. Pat. Nos. 4,940,838; 5,464,763, and the like. Methods for transforming specific dicotyledenous plants, for example, cotton, are set forth in U.S. Pat. Nos. 5,004,863; 5,159,135; and 5,846,797. Soybean transformation methods are set forth in U.S. Pat. Nos. 4,992,375; 5,416,011; 5,569,834; 5,824,877; 6,384,301 and in EP 0301749B1 may be used. Transformation methods may include direct and indirect methods of transformation. Suitable direct methods include polyethylene glycol induced DNA uptake, liposome-mediated transformation (U.S. Pat. No. 4,536,475), biolistic methods using the gene gun (Fromm M E et al., Bio/Technology. 8(9):833-9, 1990; Gordon-Kamm et al. Plant Cell 2:603, 1990), electroporation, incubation of dry embryos in DNA-comprising solution, and microinjection. In the case of these direct transformation methods, the plasmids used need not meet any particular requirements. Simple plasmids, such as those of the pUC series, pBR322, M13mp series, pACYC184 and the like can be used. If intact plants are to be regenerated from the transformed cells, an additional selectable marker gene is preferably located on the plasmid. The direct transformation techniques are equally suitable for dicotyledonous and monocotyledonous plants.

Transformation can also be carried out by bacterial infection by means of Agrobacterium (for example EP 0 116 718), viral infection by means of viral vectors (EP 0 067 553; U.S. Pat. No. 4,407,956; WO 95/34668; WO 93/03161) or by means of pollen (EP 0 270 356; WO 85/01856; U.S. Pat. No. 4,684,611). *Agrobacterium* based transformation techniques (especially for dicotyledonous plants) are well known in the art. The *Agrobacterium* strain (e.g., *Agrobacterium tumefaciens* or *Agrobacterium rhizogenes*) comprises a plasmid (Ti or Ri plasmid) and a T-DNA element which is transferred to the plant following infection with *Agrobacterium*. The T-DNA (transferred DNA) is integrated into the genome of the plant cell. The T-DNA may be localized on the Ri- or Ti-plasmid or is separately comprised in a so-called binary vector. Methods for the *Agrobacterium*-mediated transformation are described, for example, in Horsch R B et al. (1985) Science 225:1229. The *Agrobacterium*-mediated transformation is best suited to dicotyledonous plants but has also been adapted to monocotyledonous plants. The transformation of plants by Agrobacteria is described in, for example, White F F, Vectors for Gene Transfer in Higher Plants, Transgenic Plants, Vol. 1, Engineering and Utilization, edited by S. D. Kung and R. Wu, Academic Press, 1993, pp. 15-38; Jenes B et al. Techniques for Gene Transfer, Transgenic Plants, Vol. 1, Engineering and Utilization, edited by S. D. Kung and R. Wu, Academic Press, 1993, pp. 128-143; Potrykus (1991) Annu Rev Plant Physiol Plant Molec Biol 42:205-225. Transformation may result in transient or stable transformation and expression. Although a nucleotide sequence of the present invention can be inserted into any plant and plant cell falling within these broad classes, it is particularly useful in crop plant cells.

The transgenic plants of the invention may be crossed with similar transgenic plants or with transgenic plants lacking the nucleic acids of the invention or with non-transgenic plants, using known methods of plant breeding, to prepare seeds. Further, the transgenic plant cells or plants of the present invention may comprise, and/or be crossed to another transgenic plant that comprises one or more nucleic acids, thus creating a "stack" of transgenes in the plant and/or its progeny. The seed is then planted to obtain a crossed fertile transgenic plant comprising the nucleic acid of the invention. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants. The seeds of this invention can be harvested from fertile transgenic plants and be used to grow progeny generations of transformed plants of this invention including hybrid plant lines comprising the recombinant nucleic acid comprising at least 19 contiguous nucleotides of the target SMT1-gene.

In one embodiment the transgenic is a legume, preferably selected from the group consisting of beans, soya, pea, clover, kudzu, lucerne, lentils, lupins, vetches, and/or groundnut.

According to the present invention, the introduced recombinant nucleic acid may be maintained in the plant cell stably if it is incorporated into a non-chromosomal autonomous replicon or integrated into the plant chromosomes. Alternatively, the introduced recombinant nucleic acid may be present on an extra-chromosomal non-replicating vector construct and be transiently expressed or transiently active. Whether present in an extra-chromosomal non-replicating vector construct or a vector construct that is integrated into a chromosome, the recombinant nucleic acid preferably resides in a plant expression cassette. A plant expression cassette preferably contains regulatory sequences capable of driving gene expression in plant cells that are operatively linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984, EMBO J. 3:835) or functional equivalents thereof, but also all other terminators functionally active in plants are suitable. As plant gene expression is very often not limited on transcriptional levels, a plant expression cassette preferably contains other operatively linked sequences like translational enhancers such as the overdrive-sequence containing the 5'-untranslated leader sequence from tobacco mosaic virus enhancing the polypeptide per RNA ratio (Gallie et al., 1987, Nucl. Acids Research 15:8693-8711). Examples of plant expression vectors include those detailed in: Becker, D. et al., 1992, New plant binary vectors with selectable markers located proximal to the left border, Plant Mol. Biol. 20:1195-1197; Bevan, M. W., 1984, Binary Agrobacterium vectors for plant transformation, Nucl. Acid. Res. 12:8711-8721; and Vectors for Gene Transfer in Higher Plants; in: Transgenic Plants, Vol. 1, Engineering and Utilization, eds.: Kung and R. Wu, Academic Press, 1993, S. 15-38.

According to the present invention the target nucleic acid is capable to reduce the protein quantity or function of the SMT1-protein in plants cell and/or the fungus. In preferred embodiments, the decrease in the protein quantity or function of the SMT1-protein takes place in a constitutive or tissue-specific manner. In especially preferred embodiments, an essentially pathogen-induced decrease in the protein quantity or protein function takes place, for example by recombinant expression of the target nucleic acid under the control of a fungal-induceable promoter. In particular, the the expression of the target nucleic acid takes place on fungal infected sites, where, however, preferably the expression of the target nucleic acid sequence remains essentially unchanged in tissues not infected by fungus. In preferred embodiments, the protein amount of the SMT1 protein in the plant and/or the fungus is reduced by at least 10%, at least 20%, at least 30%, at least 40%, at least 50%, at least 60%, at least 70%, at least 80%, at least 90%, or at least 95% or more in comparison to a wild type plant that is not transformed with the target nucleic acid. Preferably the wild type plant is a plant of a similar, more preferably identical genotype as the plant transformed with the target nucleic acid.

Preferably term "SMT1-protein" means fungal steroyl-methyl-transferase-proteins including any homolog of the sterol methyl transferase. In particular, the term SMT1-protein refers to a protein having at least 60% identity with SEQ-ID-No. 5. In one embodiment homologues of the SMT1-protein have at least 70%, preferably of at least 80%, especially preferably of at least 90%, quite especially preferably of at least 95%, quite especially preferably of at least 98% or 100% identity to SEQ-ID-S preferably over the entire protein region.

The present invention further provides the use of the vector construct according to the present invention for the transformation of plants to provide fungal resistant plants.

The fungal pathogens or fungus-like pathogens (such as, for example, Chromista) preferably belong to the group comprising Plasmodiophoramycota, Oomycota, Ascomycota, Chytridiomycetes, Zygomycetes, Basidiomycota and/or Deuteromycetes (Fungi imperfecti). Pathogens which may be mentioned by way of example, but not by limitation, are those detailed in Tables 1 to 4, and the diseases which are associated with them.

TABLE 1

Diseases caused by biotrophic phytopathogenic fungi

| Disease | Pathogen |
|---|---|
| Leaf rust | *Puccinia recondita* |
| Yellow rust | *P. striiformis* |
| Powdery mildew | *Erysiphe graminis/Blumeria graminis* |
| Rust (common corn) | *Puccinia sorghi* |
| Rust (Southern corn) | *Puccinia polysora* |
| Tobacco leaf spot | *Cercospora nicotianae* |
| Rust (soybean) | *Phakopsora pachyrhizi*, *P. meibomiae* |
| Rust (tropical corn) | *Physopella pallescens*, *P. zeae* = *Angiopsora zeae* |

TABLE 2

Diseases caused by necrotrophic and/or hemibiotrophic fungi and Oomycetes

| Disease | Pathogen |
|---|---|
| Plume blotch | *Septoria* (*Stagonospora*) *nodorum* |
| Leaf blotch | *Septoria tritici* |
| Ear fusarioses | *Fusarium* spp. |
| Eyespot | *Pseudocercosporella herpotrichoides* |
| Smut | *Ustilago* spp. |
| Late blight | *Phytophthora infestans* |
| Bunt | *Tilletia caries* |
| Take-all | *Gaeumannomyces graminis* |
| Anthrocnose leaf blight | *Colletotrichum graminicola* (teleomorph: |
| Anthracnose stalk rot | *Glomerella graminicola* Politis); *Glomerella tucumanensis* (anamorph: *Glomerella falcatum* Went) |
| *Aspergillus* ear and kernel rot | *Aspergillus flavus* |
| Banded leaf and sheath spot ("Wurzeltöter") | *Rhizoctonia solani* Kuhn = *Rhizoctonia microsclerotia* J. Matz (telomorph: *Thanatephorus cucumeris*) |

TABLE 2-continued

| Diseases caused by necrotrophic and/or hemibiotrophic fungi and Oomycetes | |
|---|---|
| Disease | Pathogen |
| Black bundle disease | *Acremonium strictum* W. Gams = *alosporium acremonium* Auct. non Corda |
| Black kernel rot | *Lasiodiplodia theobromae* = *Botryodiplodia theobromae* |
| Borde blanco | *Marasmiellus* sp. |
| Brown spot (black spot, stalk rot) | *Physoderma maydis* |
| *Cephalosporium* kernel rot | *Acremonium strictum* = *Cephalosporium acremonium* |
| Charcoal rot | *Macrophomina phaseolina* |
| *Corticium* ear rot | *Thanatephorus cucumeris* = *Corticium sasakii* |
| *Curvularia* leaf spot | *Curvularia clavata*, *C. eragrostidis*, = *C. maculans* (teleomorph: *Cochliobolus eragrostidis*), *Curvularia inaequalis*, *C. intermedia* (teleomorph: *Cochliobolus intermedius*), *Curvularia lunata* (teleomorph: *Cochliobolus lunatus*), *Curvularia pallescens* (teleomorph: *Cochliobolus pallescens*), *Curvularia senegalensis*, *C. tuberculata* (teleomorph: *Cochliobolus tuberculatus*) |
| *Didymella* leaf spot | *Didymella exitalis* |
| *Diplodia* ear and stalk rot | *Diplodia frumenti* (teleomorph: *Botryosphaeria festucae*) |
| *Diplodia* ear and stalk rot, seed rot and seedling blight | *Diplodia maydis* = *Stenocarpella maydis* |
| *Diplodia* leaf spot or streak | *Stenocarpella macrospora* = *Diplodialeaf macrospora* |
| Brown stripe downy mildew | *Sclerophthora rayssiae* var. *zeae* |
| Crazy top downy mildew | *Sclerophthora macrospora* = *Sclerospora macrospora* |
| Green ear downy mildew (*graminicola* downy mildew) | *Sclerospora graminicola* |
| Dry ear rot (cob, kernel and stalk rot) | *Nigrospora oryzae* (teleomorph: *Khuskia oryzae*) |
| Ear rots (minor) | *Alternaria alternata* = *A. tenuis*, *Aspergillus glaucus*, *A. niger*, *Aspergillus* spp., *Botrytis cinerea* (teleomorph: *Botryotinia fuckeliana*), *Cunninghamella* sp., *Curvularia pallescens*, *Doratomyces stemonitis* = *Cephalotrichum stemonitis*, *Fusarium culmorum*, *Gonatobotrys simplex*, *Pithomyces maydicus*, *Rhizopus microsporus* Tiegh., *R. stolonifer* = *R. nigricans*, *Scopulariopsis brumptii* |
| Ergot (horse's tooth) | *Claviceps gigantea* (anamorph: *Sphacelia* sp.) |
| Eyespot | *Aureobasidium zeae* = *Kabatiella zeae* |
| *Fusarium* ear and stalk rot | *Fusarium subglutinans* = *F. moniliforme* var. *subglutinans* |
| *Fusarium* kernel, root and stalk rot, seed rot and seedling blight | *Fusarium moniliforme* (teleomorph: *Gibberella fujikuroi*) |
| *Fusarium* stalk rot, seedling root rot | *Fusarium avenaceum* (teleomorph: *Gibberella avenacea*) |
| *Gibberella* ear and stalk rot | *Gibberella zeae* (anamorph: *Fusarium graminearum*) |
| Gray ear rot | *Botryosphaeria zeae* = *Physalospora zeae* (anamorph: *Macrophoma zeae*) |
| Gray leaf spot (*Cercospora* leaf spot) | *Cercospora sorghi* = *C. sorghi* var. *maydis*, *C. zeae-maydis* |
| *Helminthosporium* root rot | *Exserohilum pedicellatum* = *Helminthosporium pedicellatum* (teleomorph: *Setosphaeria pedicellata*) |
| *Hormodendrum* ear rot (*Cladosporium* rot) | *Cladosporium cladosporioides* = *Hormodendrum cladosporioides*, *C. herbarum* (teleomorph: *Mycosphaerella tassiana*) |
| Leaf spots, minor | *Alternaria alternata*, *Ascochyta maydis*, *A. tritici*, *A. zeicola*, *Bipolaris victoriae* = *Helminthosporium victoriae* (teleomorph: *Cochliobolus victoriae*), *C. sativus* (anamorph: *Bipolaris sorokiniana* = *H. sorokinianum* = *H. sativum*), *Epicoccum nigrum*, |

TABLE 2-continued

| Diseases caused by necrotrophic and/or hemibiotrophic fungi and Oomycetes | |
|---|---|
| Disease | Pathogen |
| | *Exserohilum prolatum* = *Drechslera prolata* (teleomorph: *Setosphaeria prolata*) *Graphium penicillioides*, *Leptosphaeria maydis*, *Leptothyrium zeae*, *Ophiosphaerella herpotricha*, (anamorph: *Scolecosporiella* sp.), *Paraphaeosphaeria michotii*, *Phoma* sp., *Septoria zeae*, *S. zeicola*, *S. zeina* |
| Northern corn leaf blight (white blast, crown stalk rot, stripe) | *Setosphaeria turcica* (anamorph: *Exserohilum turcicum* = *Helminthosporium turcicum*) |
| Northern corn leaf spot *Helminthosporium* ear rot (race 1) | *Cochliobolus carbonum* (anamorph: *Bipolaris zeicola* = *Helminthosporium carbonum*) |
| *Penicillium* ear rot (blue eye, blue mold) | *Penicillium* spp., *P. chrysogenum*, *P. expansum*, *P. oxalicum* |
| *Phaeocytostroma* stalk and root rot | *Phaeocytostroma ambiguum*, = *Phaeocytosporella zeae* |
| *Phaeosphaeria* leaf spot | *Phaeosphaeria maydis* = *Sphaerulina maydis* |
| *Physalospora* ear rot (*Botryosphaeria* ear rot) | *Botryosphaeria festucae* = *Physalospora zeicola* (anamorph: *Diplodia frumenti*) |
| Purple leaf sheath | Hemiparasitic bacteria and fungi |
| *Pyrenochaeta* stalk and root rot | *Phoma terrestris* = *Pyrenochaeta terrestris* |
| *Pythium* root rot | *Pythium* spp., *P. arrhenomanes*, *P. graminicola* |
| *Pythium* stalk rot | *Pythium aphanidermatum* = *P. butleri* L. |
| Red kernel disease (ear mold, leaf and seed rot) | *Epicoccum nigrum* |
| *Rhizoctonia* ear rot (sclerotial rot) | *Rhizoctonia zeae* (teleomorph: *Waitea circinata*) |
| *Rhizoctonia* root and stalk rot | *Rhizoctonia solani*, *Rhizoctonia zeae* |
| Root rots (minor) | *Alternaria alternata*, *Cercospora sorghi*, *Dictochaeta fertilis*, *Fusarium acuminatum* (teleomorph: *Gibberella acuminata*), *F. equiseti* (teleomorph: *G. intricans*), *F. oxysporum*, *F. pallidoroseum*, *F. poae*, *F. roseum*, *G. cyanogena*, (anamorph: *F. sulphureum*), *Microdochium bolleyi*, *Mucor* sp., *Periconia circinata*, *Phytophthora cactorum*, *P. drechsleri*, *P. nicotianae* var. *parasitica*, *Rhizopus arrhizus* |
| *Rostratum* leaf spot (*Helminthosporium* leaf disease, ear and stalk rot) | *Setosphaeria rostrata*, (anamorph: *xserohilum rostratum* = *Helminthosporium rostratum*) |
| Java downy mildew | *Peronosclerospora maydis* = *Sclerospora maydis* |
| Philippine downy mildew | *Peronosclerospora philippinensis* = *Sclerospora philippinensis* |
| *Sorghum* downy mildew | *Peronosclerospora sorghi* = *Sclerospora sorghi* |
| *Spontaneum* downy mildew | *Peronosclerospora spontanea* = *Sclerospora spontanea* |
| Sugarcane downy mildew | *Peronosclerospora sacchari* = *Sclerospora sacchari* |
| *Sclerotium* ear rot (southern blight) | *Sclerotium rolfsii* Sacc. (teleomorph: *Athelia rolfsii*) |
| Seed rot-seedling blight | *Bipolaris sorokiniana*, *B. zeicola* = *Helminthosporium carbonum*, *Diplodia maydis*, *Exserohilum pedicillatum*, *Exserohilum turcicum* = *Helminthosporium turcicum*, *Fusarium avenaceum*, *F. culmorum*, *F. moniliforme*, *Gibberella zeae* (anamorph: *F. graminearum*), *Macrophomina phaseolina*, *Penicillium* spp., *Phomopsis* sp., *Pythium* spp., *Rhizoctonia solani*, *R. zeae*, *Sclerotium rolfsii*, *Spicaria* sp. |
| *Selenophoma* leaf spot | *Selenophoma* sp. |
| Sheath rot | *Gaeumannomyces graminis* |
| Shuck rot | *Myrothecium gramineum* |
| Silage mold | *Monascus purpureus*, *M ruber* |
| Smut, common | *Ustilago zeae* = *U. maydis* |
| Smut, false | *Ustilaginoidea virens* |
| Smut, head | *Sphacelotheca reiliana* = *Sporisorium holcisorghi* |
| Southern corn leaf blight and stalk rot | *Cochliobolus heterostrophus* (anamorph: *Bipolaris maydis* = *Helminthosporium maydis*) |

TABLE 2-continued

| Diseases caused by necrotrophic and/or hemibiotrophic fungi and Oomycetes | |
|---|---|
| Disease | Pathogen |
| Southern leaf spot | *Stenocarpella macrospora = Diplodia macrospora* |
| Stalk rots (minor) | *Cercospora sorghi*, *Fusarium episphaeria*, *F. merismoides*, *F. oxysporum* Schlechtend, *F. poae*, *F. roseum*, *F. solani* (teleomorph: *Nectria haematococca*), *F. tricinctum*, *Mariannaea elegans*, *Mucor* sp., *Rhopographus zeae*, *Spicaria* sp. |
| Storage rots | *Aspergillus* spp., *Penicillium* spp. and *weitere Pilze* |
| Tar spot | *Phyllachora maydis* |
| *Trichoderma* ear rot and root rot | *Trichoderma viride = T. lignorum* teleomorph: *Hypocrea* sp. |
| White ear rot, root and stalk rot | *Stenocarpella maydis = Diplodia zeae* |
| Yellow leaf blight | *Ascochyta ischaemi*, *Phyllosticta maydis* (teleomorph: *Mycosphaerella zeae-maydis*) |
| Zonate leaf spot | *Gloeocercospora sorghi* |

TABLE 4

| Diseases caused by fungi and Oomycetes with unclear classification regarding biotrophic, hemibiotrophic or necrotrophic behavior | |
|---|---|
| Disease | Pathogen |
| *Hyalothyridium* leaf spot | *Hyalothyridium maydis* |
| Late wilt | *Cephalosporium maydis* |

The following are especially preferred:

Plasmodiophoromycota such as *Plasmodiophora brassicae* (clubroot of crucifers), *Spongospora subterranean, Polymyxa graminis*, Oomycota such as *Bremia lactucae* (downy mildew of lettuce), *Peronospora* (downy mildew) in snapdragon (*P. antirrhini*), onion (*P. destructor*), spinach (*P. effuse*), soybean (*P. manchurica*), tobacco ("blue mold"; *P. tabacina*) alfalfa and clover (*P. trifolium*), *Pseudoperonospora humuli* (downy mildew of hops), *Plasmopara* (downy mildew in grapevines) (*P. viticola*) and sunflower (*P. halstedii*), *Sclerophthora macrospora* (downy mildew in cereals and grasses), *Pythium* (for example damping-off of Beta beet caused by *P. debaryanum*), *Phytophthora infestans* (late blight in potato and in tomato and the like), *Albugo* spec.

Ascomycota such as *Microdochium nivale* (snow mold of rye and wheat), *Fusarium graminearum, Fusarium culmorum* (partial ear sterility mainly in wheat), *Fusarium oxysporum*,(*Fusarium wilt* of tomato), *Blumeria graminis* (powdery mildew of barley (f.sp. *hordei*) and wheat (f.sp. *tritici*)), *Erysiphe pisi* (powdery mildew of pea), *Nectria galligena* (*Nectria canker* of fruit trees), *Uncinula necator* (powdery mildew of grapevine), *Pseudopeziza tracheiphila* (red fire disease of grapevine), *Claviceps purpurea* (ergot on, for example, rye and grasses), *Gaeumannomyces graminis* (take-all on wheat, rye and other grasses), *Magnaporthe grisea, Pyrenophora graminea* (leaf stripe of barley), *Pyrenophora teres* (net blotch of barley), *Pyrenophora tritici-repentis* (leaf blight of wheat), *Venturia inaequalis* (apple scab), *Sclerotinia sclerotium* (stalk break, stem rot), *Pseudopeziza medicaginis* (leaf spot of alfalfa, white and red clover).

Basidiomycetes such as *Typhula incarnata* (typhula blight on barley, rye, wheat), *Ustilago maydis* (blister smut on maize), *Ustilago nuda* (loose smut on barley), *Ustilago tritici* (loose smut on wheat, spelt), *Ustilago avenae* (loose smut on oats), *Rhizoctonia solani* (*rhizoctonia* root rot of potato), *Sphacelotheca* spp. (head smut of sorghum), *Melampsora lini* (rust of flax), *Puccinia graminis* (stem rust of wheat, barley, rye, oats), *Puccinia recondita* (leaf rust on wheat), *Puccinia dispersa* (brown rust on rye), *Puccinia hordei* (leaf rust of barley), *Puccinia coronata* (crown rust of oats), *Puccinia striiformis* (yellow rust of wheat, barley, rye and a large number of grasses), *Uromyces appendiculatus* (brown rust of bean), *Sclerotium rolfsii* (root and stem rots of many plants).

Deuteromycetes (Fungi imperfecti) such as *Septoria* (*Stagonospora*) *nodorum* (glume blotch) of wheat (*Septoria tritici*), *Pseudocercosporella herpotrichoides* (eyespot of wheat, barley, rye), *Rynchosporium secalis* (leaf spot on rye and barley), *Alternaria solani* (early blight of potato, tomato), *Phoma betae* (blackleg on Beta beet), *Cercospora beticola* (leaf spot on Beta beet), *Alternaria brassicae* (black spot on oilseed rape, cabbage and other crucifers), *Verticillium dahliae* (*verticillium wilt*), *Colletotrichum lindemuthianum* (bean anthracnose), *Phoma lingam* (blackleg of cabbage and oilseed rape), *Botrytis cinerea* (grey mold of grapevine, strawberry, tomato, hops and the like).

Especially preferred are biotrophic pathogens, among which in particular hemibiotrophic pathogens, i.e. *Phakopsora pachyrhizi* and/or those pathogens which have essentially a similar infection mechanism as *Phakopsora pachyrhizi*, as described herein. Particularly preferred are pathogens from the group Uredinales (rusts), among which in particular the Melompsoraceae. Especially preferred are *Phakopsora pachyrhizi* and/or *Phakopsora meibomiae.*

Harvestable parts of the transgenic plant according to the present invention are part of the invention. The harvestable parts may be seeds, roots, leaves and/or flowers comprising the SMT1-gene, the complementary SMT1-gene and/or a part thereof. Preferred parts of soy plants are soy beans comprising the transgenic SMT1-gene.

Products derived from transgenic plant according to the present invention, parts thereof or harvestable parts thereof are part of the invention. A preferred product is soybean meal, soybean oil, wheat meal, corn starch, corn oil, corn meal, rice meal, canola oil and/or potato starch.

The present invention also includes methods for the production of a product comprising a) growing the plants of the invention and b) producing said product from or by the plants of the invention and/or parts thereof, e.g. seeds, of these plants. In a further embodiment the method comprises the steps a) growing the plants of the invention, b) removing the harvestable parts as defined above from the plants and c) producing said product from or by the harvestable parts of the invention.

In one embodiment the method for the production of a product comprises a) growing the plants of the invention or obtainable by the methods of invention and b) producing said product from or by the plants of the invention and/or parts, e.g. seeds, of these plants.

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In one embodiment the products produced by said methods of the invention are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one ore more agricultural products to a large extent.

All definitions given to terms used in specific type of category (method for producing a plant and/or part thereof resistant to fungus, transgenic plant cell, vector construct, use of the vector construct etc.) may be also applicable for the other categories.

FIGURES

FIG. 1 shows the full-length-sequence of the SMT1-gene from *Phakopsora pachyrhizi* having SEQ-ID-No.1.

FIG. 2A shows the sequence of the SMT1-gene from *Phakopsora pachyrhizi* used for primer design and construct generation having SEQ-ID-No.2.

FIG. 2B shows a partial sequence of FIG. 1 (SEQ-ID-3).

FIG. 3 shows the sequence of one vector construct useful according to the present invention (parsley ubiquitin promoter: SMT1 fragment antisense orientation: spacer sequence: SMT1 fragment sense orientation: nopaline synthase promoter)(SEQ-ID-No.4).

FIG. 4 shows the sequence of the SMT1-protein (SEQ-ID-5).

FIG. 5 shows single sequences which are part of the vector construct of FIG. 3.

FIG. 7 shows the scoring system used to determine the level of resistance of wildtype and transgenic (SMT1 RNAi) soybean plants against the soybean rust fungus *P. pachyrhizi*.

Figure 8:
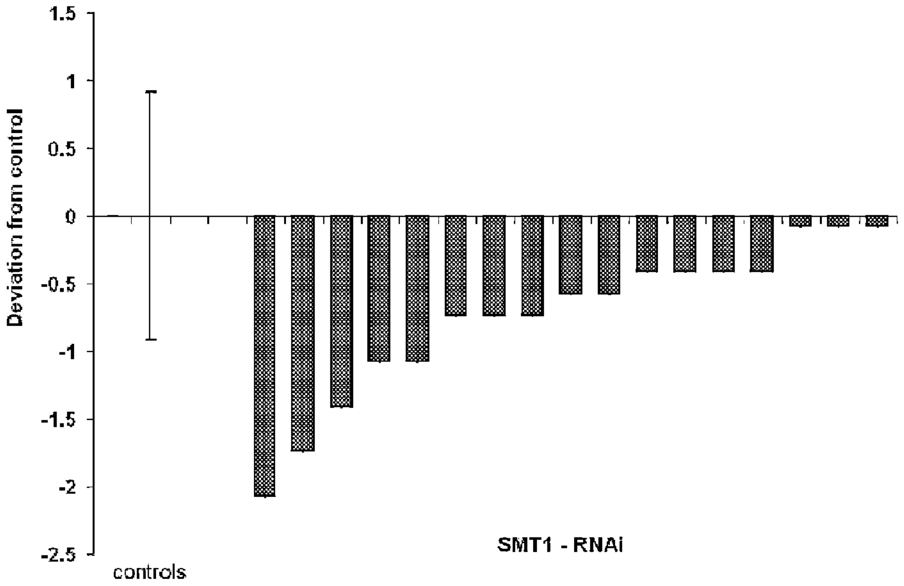

FIG. 8 shows the result of the scoring of 17 transgenic soybean events expressing the SMT1 RNAi construct. The average scoring of the wildtype controls was 4.1 (which can be translated to approximately 50% diseased leaf area. The average scoring of the controls was set to zero. For each transgenic soybean event (expressing the SMT1 RNAi construct) 1-3 clones were scored. The bars represent the deviation of transgenic soybean events (expressing the SMT1 RNAi construct) the from the average of wild type controls.

EXAMPLES

The following examples are not intended to limit the scope of the claims to the invention, but are rather intended to be exemplary of certain embodiments. Any variations in the exemplified methods that occur to the skilled artisan are intended to fall within the scope of the present invention.

Example 1

General methods

The chemical synthesis of oligonucleotides can be affected, for example, in the known fashion using the phosphoamidite method (Voet, Voet, 2nd Edition, Wiley Press New York, pages 896-897). The cloning steps carried out for the purposes of the present invention such as, for example, restriction cleavages, agarose gel electrophoresis, purification of DNA fragments, transfer of nucleic acids to nitrocellulose and nylon membranes, linking DNA fragments, transformation of *E. coli* cells, bacterial cultures, phage multiplication and sequence analysis of recombinant DNA, are carried out as described by Sambrook et al. Cold Spring Harbor Laboratory Press (1989), ISBN 0-87969-309-6. The sequencing of recombinant DNA molecules is carried out with an MWG-Licor laser fluorescence DNA sequencer following the method of Sanger (Sanger et al., Proc. Natl. Acad. Sci. USA 74, 5463 (1977)).

Example 2

Cloning of RNAi Construct RNAi Hairpin Structure

Figure 6:
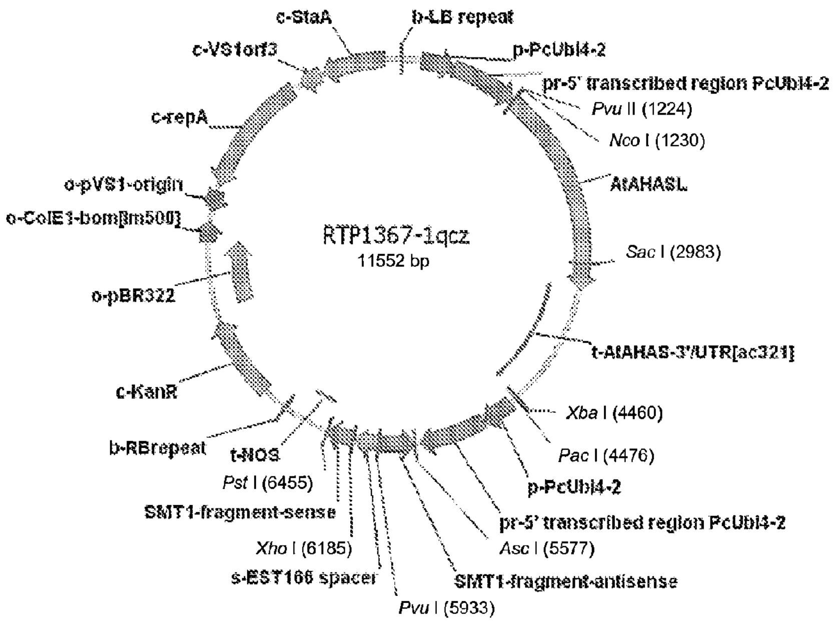
FIG. 6 shows a schema of one vector construct useful according to the present invention

The RNAi-construct (FIGS. 3 and 6) was prepared as follows: By PCR based amplification AscI and AatII restriction sites were introduced on the first stem (antisense; from position 148 to 454 relative to SEQ ID2) and SbfI and XhoI sites were introduced on the second stem (sense, Position 199-454) both in the 5'-3' strand "sense" orientation (relative zu SEQ 1D2). For the introduction of the resctriction sites the nucleic acid of the first stem having SEQ-1D-No.7 was amplified using using primers having SEQ-ID No. 11 and 12. For the introduction of the resctriction sites the nucleic acid of the second stem having SEQ-ID-No.9 was amplified using using primers having SEQ-ID No 13 and 14. Both fragments were cloned using the TOPO cloning system (TOPO® TA Cloning® Kit Invitrogen). Both fragments were sequenced. Each stem was cut with the respective enzymes and gel purified.

Likewise, the spacer having SEQ-ID-No. 8 (AatlI::Stops block:EST166::Stops Block::XhoI) was cloned FIG. 3). It was cut with Aatl I and XhoI and gel purified.

As binary base vector a binary vector was used which is composed of: (1) a Kanamycin resistance cassette for bacterial selection (2) a pVS1 origin for replication in Agorbacteria (3) a pBR322 origin of replication for stable maintenance in *E. coli* and (4) between the right and left border an AHAS selection marker under control of a pcUbi-promoter and an Ubi-promoter:MCS::t-Nos cassette for cloning of the target gene (cf. FIGS. 3 and 6). The base vector was cut within the MCS with Ascl and Sbfl and the backbone purified by gel purification.

All four fragments were ligated using T4 ligase under standard conditions and transformed into *E. coli*, mini-prepped and screened by Ascl & Sbfl digestion. A positive clone (RTP1367) was submitted to soybean transformation.

Soybean transformation

The RTP1376 construct was transformed into soybean.

Example 3

Sterilization and Germination of Soybean Seeds

Virtually any seed of any soybean variety can be employed in the method of the invention. A variety of soybean cultivar (including Jack, Williams 82, and Resnik) is appropriate for soybean transformation. Soybean seeds were sterilized in a chamber with a chlorine gas produced by adding 3.5 ml 12N HCl drop wise into 100 ml bleach (5.25% sodium hypochlorite) in a desiccator with a tightly fitting lid. After 24 to 48 hours in the chamber, seeds were removed and approximately 18 to 20 seeds were plated on solid GM medium with or without 5 μM 6-benzyl-aminopurine (BAP) in 100 mm Petri dishes. Seedlings without BAP were more elongated and roots developed, especially secondary and lateral root formation. BAP strengthened the seedling by forming a shorter and stockier seedling.

Seven-day-old seedlings grown in the light (>100 .μEinstein/$m^2$s) at 25° C. were used for explant material for the three-explant types. At this time, the seed coat was split, and the epicotyl with the unifoliate leaves had grown to, at minimum, the length of the cotyledons. The epicotyl should be at least 0.5 cm to avoid the cotyledonary-node tissue (since soybean cultivars and seed lots may vary in the developmental time a description of the germination stage is more accurate than a specific germination time).

For inoculation of entire seedlings (Method A, see example 5.1) or leaf explants (Method B, see example 5.3), the seedlings were then ready for transformation.

For method C (see example 5.4), the hypocotyl and one and a half or part of both cotyledons were removed from each seedling. The seedlings were then placed on propagation media for 2 to 4 weeks. The seedlings produced several branched shoots to obtain explants from. The majority of the explants originated from the plantlet growing from the apical bud. These explants were preferably used as target tissue.

Example 4

Growth and Preparation of Agrobacterium Culture

*Agrobacterium* cultures were prepared by streaking *Agrobacterium* (e.g. *A. tumefaciens* or *A. rhizogenes*) carrying the desired binary vector (e.g. H Klee, R Horsch, and S Rogers 1987 Agrobacterium-Mediated Plant Transformation and its Further Applications to Plant Biology; Annual Review of Plant Physiology Vol. 38: 467-486) onto solid YEP growth medium (YEP media: 10 g yeast extract. 10 g Bacto Peptone. 5 g NaCl. Adjust pH to 7.0, and bring final volume to 1 liter with H2O, for YEP agar plates add 20g Agar, autoclave) and incubating at 25° C. until colonies appeared (about 2 days). Depending on the selectable marker genes present on the Ti or Ri plasmid, the binary vector, and the bacterial chromosomes, different selection compounds were used for *A. tumefaciens* and rhizogenes selection in the YEP solid and liquid media. Various *Agrobacterium* strains can be used for the transformation method.

After approximately two days, a single colony (with a sterile toothpick) was picked and 50 ml of liquid YEP was inoculated with antibiotics and shaken at 175 rpm (25° C.) until an OD.sub.600 between 0.8-1.0 is reached (approximately 2 d). Working glycerol stocks (15%) for transformation were prepared and one-ml of *Agrobacterium* stock aliquoted into 1.5 ml Eppendorf tubes then stored at −80° C.

The day before explant inoculation, 200 ml of YEPmedia were inoculated with 5 pl to 3 ml of working Agrobacterium stock in a 500 ml Erlenmeyer flask. The flask was shaked overnight at 25 ° C. until the OD600 was between 0.8 and 1.0. Before preparing the soybean explants, the Agrobacteria were pelleted by centrifugation for 10 min at 5,500.times.g at 20° C. The pellet was resuspended in liquid CCM to the desired density (OD600 0.5-0.8) and placed at room temperature at least 30 min before use.

Example 5

Explant Preparation and Co-Cultivation (Inoculation)

5.1 Method A: Explant Preparation on the Day of Transformation.

Seedlings at this time had elongated epicotyls from at least 0.5 cm but generally between 0.5 and 2 cm. Elongated epicotyls up to 4 cm in length had been successfully employed. Explants were then prepared with: i) with or without some roots, ii) with a partial, one or both cotyledons, all preformed leaves were removed including apical meristem, and the node located at the first set of leaves was injured with several cuts using a sharp scalpel.

This cutting at the node not only induced *Agrobacterium* infection but also distributed the axillary meristem cells and damaged pre-formed shoots. After wounding and preparation, the explants were set aside in a Petri dish and subsequently co-cultivated with the liquid CCM/*Agrobacterium* mixture for 30 minutes. The explants were then removed from the liquid medium and plated on top of a sterile filter paper on 15.times.100 mm Petri plates with solid co-cultivation medium. The wounded target tissues were placed such that they are in direct contact with the medium.

5.2 Modified Method A: Epicotyl Explant Preparation

Soybean epicotyl segments prepared from 4 to 8 d old seedlings were used as explants for regeneration and transformation. Seeds of soybean cv L00106CN, 93-41131 and Jack were germinated in 1/10 MS salts or a similar composition medium with or without cytokinins for 4.about.8 d. Epicotyl explants were prepared by removing the cotyledonary node and stem node from the stem section. The epicotyl was cut into 2 to 5 segments. Especially preferred were segments attached to the primary or higher node comprising axillary meristematic tissue.

The explants were used for *Agrobacterium* infection. *Agrobacterium* AGL1(Lazo G R, Stein P A, Ludwig R A A DNA transformation-competent Arabidopsis genomic library in *Agrobacterium*. Biotechnology (N Y) 1991 Oct;9(10):963-967) harboring a plasmid with the GUS marker gene and the AHAS, bar or dsdA selectable marker gene was cultured in LB medium with appropriate antibiotics overnight, harvested and resuspended in a inoculation medium with acetosyringone. Freshly prepared epicotyl segments were soaked in the *Agrobacterium* suspension for 30 to 60 min and then the explants were blotted dry on sterile filter papers. The inoculated explants were then cultured on a co-culture medium with L-cysteine and DTT (Dithiothreitol) and other chemicals such as acetosyringone for enhancing T-DNA delivery for 2 to 4 d. The infected epicotyl explants were then placed on a shoot induction medium with selection agents such as imazapyr (for AHAS gene), glufosinate (for bar gene), or D-serine (for dsdA gene). The regenerated shoots were subcultured on elongation medium with the selective agent.

For regeneration of transgenic plants the segments were then cultured on a medium with cytokinins such as BAP (6-benzylaminopurine), TDZ (thidiazuron) and/or Kinetin for shoot induction. After 4 to 8 weeks, the cultured tissues were transferred to a medium with lower concentration of cytokinin for shoot elongation. Elongated shoots were transferred to a medium with auxin for rooting and plant development. Multiple shoots were regenerated.

5.3 Method B: Leaf Explants

For the preparation of the leaf explant the cotyledon was removed from the hypocotyl. The cotyledons were separated from one another and the epicotyl is removed. The primary leaves, which consist of the lamina, the petiole, and the stipules, were removed from the epicotyl by carefully cutting at the base of the stipules such that the axillary meristems were included on the explant. To wound the explant as well as to stimulate de novo shoot formation, any pre-formed shoots were removed and the area between the stipules was cut with a sharp scalpel 3 to 5 times.

The explants are either completely immersed or the wounded petiole end dipped into the *Agrobacterium* suspension immediately after explant preparation. After inoculation, the explants are blotted onto sterile filter paper to remove excess *Agrobacterium* culture and place explants with the wounded side in contact with a round 7 cm Whatman paper overlaying the solid CCM medium (see above). This filter paper prevents A. tumefaciens overgrowth on the soybean explants. Wrap five plates with Parafilm™. "M" (American National Can, Chicago, Ill., USA) and incubate for three to five days in the dark or light at 25° C.

5.4 Method C: Propagated Axillary Meristem

For the preparation of the propagated axillary meristem explant propagated 3-4 week-old plantlets were used. Axillary meristem explants could be pre-pared from the first to the fourth node. An average of three to four explants could be obtained from each seedling. The explants were prepared from plantlets by cutting 0.5 to 1.0 cm below the axillary node on the internode and removing the petiole and leaf from the explant. The tip where the axillary meristems lie was cut with a scalpel to induce de novo shoot growth and allow access of target cells to the *Agrobacterium*. Therefore, a 0.5 cm explant included the stem and a bud.

Once cut, the explants were immediately placed in the *Agrobacterium* suspension for 20 to 30 minutes. After inoculation, the explants were blotted onto sterile filter paper to remove excess *Agrobacterium* culture then placed almost completely immersed in solid coculture media CCM (see Olhoft et al 2007 A novel *Agrobacterium* rhizogenes-mediated transformation method of soybean using primary-node explants from seedlings in Vitro Cell. Dev. Biol.—Plant (2007) 43:536-549) or on top of a round 7 cm filter paper overlaying the solid CCM, depending on the *Agrobacterium* strain. This filter paper prevented *Agrobacterium* overgrowth on the soybean explants. Plates were wrapped with Parafilm™. "M" (American National Can, Chicago, Ill., USA) and incubated for two to three days in the dark at 25° C.

Example 6

Shoot Induction

After 3 to 5 days co-cultivation in the dark at 25° C., the explants were rinsed in liquid shoot induction medium (SIM, see Olhoft et al 2007 A novel *Agrobacterium* rhizogenes-mediated transformation method of soybean using primary-node explants from seedlings In Vitro Cell. Dev. Biol.—Plant (2007) 43:536-549; to remove excess *Agrobacterium*) or Modwash medium (1×5 major salts, 1×5minor salts, 1× MSIII iron, 3% Sucrose, 1×5 vitamins, 30 mM MES, 350 mg/L Timentin™ pH 5.6, WO 2005/121345) (Method C) and blotted dry on sterile filter paper (to prevent damage especially on the lamina) before placing on the solid SIM medium. The approximately 5 explants (Method A) or 10 to 20 (Methods B and C) explants were placed such that the target tissue was in direct contact with the medium. During the first 2 weeks, the explants could be cultured with or without selective medium. Preferably, explants were transferred onto SIM without selection for one week.

For leaf explants (Method B), the explant should be placed into the medium such that it is perpendicular to the surface of the medium with the petiole imbedded into the medium and the lamina out of the medium.

For propagated axillary meristem (Method C), the explant was placed into the medium such that it iwas parallel to the surface of the medium (basipetal) with the explant partially embedded into the medium.

Wrap plates with Scotch 394 venting tape (3M, St. Paul, Minn., USA) were placed in a growth chamber for two weeks with a temperature averaging 25° C. under 18 h light/6 h dark cycle at 70-100 pE/m$^2$s. The explants remained on the SIM medium with or without selection until de novo shoot growth occured at the target area (e.g., axillary meristems at the first node above the epicotyl). Transfers to fresh medium can occur during this time. Explants were transferred from the SIM with or without selection to SIM with selection after about one week. At this time, there was considerable de novo shoot development at the base of the petiole of the leaf explants in a variety of SIM (Method B), at the primary node for seedling explants (Method A), and at the axillary nodes of propagated explants (Method C).

Preferably, all shoots formed before transformation were removed up to 2 weeks after co-cultivation to stimulate new growth from the meristems. This helped to reduce chimerism in the primary transformant and increase amplification of transgenic meristematic cells. During this time the explant may or may not be cut into smaller pieces (i.e. detaching the node from the explant by cutting the epicotyl).

Example 7

Shoot Elongation

After 2 to 4 weeks (or until a mass of shoots was formed) on SIM medium (preferably with selection), the explants were transferred to SEM medium (shoot elongation medium, see Olhoft et al 2007 A novel *Agrobacterium* rhizogenes-mediated transformation method of soybean using primary-node explants from seedlingsln Vitro Cell. Dev. Biol.—Plant (2007) 43:536-549) that stimulates shoot elongation of the shoot primordia. This medium may or may not contain a selection compound.

After every 2 to 3 weeks, the explants were transfered to fresh SEM medium (preferably containing selection) after carefully removing dead tissue. The explants should hold together and not fragment into pieces and retain somewhat healthy. The explants were continued to be transferred until the explant dies or shoots elongate. Elongated shoots >3 cm were removed and placed into RM medium (see Olhoft et al 2007 A novel *Agrobacterium* rhizogenes-mediated transformation method of soybean using primary-node explants from seedlings In Vitro Cell. Dev. Biol.—Plant (2007) 43:536-549) for about 1 week (Method A and B), or about 2 to 4 weeks depending on the cultivar (Method C) at which time roots began to form. In the case of explants with roots, they were transferred directly into soil. Rooted shoots were transferred to soil and hardened in a growth chamber for 2 to 3 weeks before transferring to the greenhouse. Regenerated plants obtained using this method were fertile and produced on average 500 seeds per plant.

Transient GUS expression after 5 days of co-cultivation with *Agrobacterium tumefaciens* was widespread on the seedling axillary meristem explants especially in the regions wounding during explant preparation (Method A). Explants were placed into shoot induction medium without selection to see how the primary-node responds to shoot induction and regeneration. Thus far, greater than 70% of the explants were formed new shoots at this region . Expression of the GUS gene was stable after 14 days on SIM, implying integration of the T-DNA into the soybean genome. In addition, preliminary experiments resulted in the formation of GUS positive shoots forming after 3 weeks on SIM.

[For Method C, the average regeneration time of a soybean plantlet using the propagated axillary meristem protocol was 14 weeks from explant inoculation. Therefore, this method has a quick regeneration time that leads to fertile, healthy soybean plants.

8.1. Recovery of clones 2-3 clones per T0 event were potted into small 6 cm pots. For recovery the clones were kept for 12-18 days in the Phytochamber (16 h-day-und 8 h-night-Rhythm at a temeperature of 16° bis 22° C. und a humidty of 75% were grown).

8.2 Inoculation

The soybean rust fungus was a wild isolate from Brazil. The plants were inoculated with *P. pachyrhizi.*

In order to obtain appropriate spore material for the inoculation, soybean leaves which had been infected with soybean rust 15-20 days ago, were taken 2-3 days before the inoculation and transferred to agar plates (1% agar in H2O). The leaves were placed with their upper side onto the agar, which allowed the fungus to grow through the tissue and to produce very young spores. For the inoculation solution, the spores were knocked off the leaves and were added to a Tween-H20 solution. The counting of spores was performed under a light microscope by means of a Thoma counting chamber. For the inoculation of the plants, the spore suspension was added into a compressed-air operated spray flask and applied uniformly onto the plants or the leaves until the leaf surface is well moisturized. For the microscopy, a density of 10×105 spores/ml is used. The inoculated plants were placed for 24 hours in a greenhouse chamber with an average of 22° C. and >90% of air humidity. The inoculated leaves were incubated under the same conditions in a closed Petri dish on 0.5% plant agar. The following cultivation was performed in a chamber with an average of 25° C. and 70% of air humidity.

8.3 Microscopical Screening

For the evaluation of the pathogen development, the inoculated leaves of plants were stained with aniline blue.

The aniline blue staining served for the detection of fluorescent substances. During the defense reactions in host interactions and non-host interactions, substances such as phenols, callose or lignin accumulated or were produced and were incorporated at the cell wall either locally in papillae or in the whole cell (hypersensitive reaction, HR). Complexes were formed in association with aniline blue, which lead e.g. in the case of callose to yellow fluorescence. The leaf material was transferred to falcon tubes or dishes containing destaining solution II (ethanol/acetic acid 6/1) and was incubated in a water bath at 90° C. for 10-15 minutes. The destaining solution II was removed immediately thereafter, and the leaves were washed 2× with water. For the staining, the leaves were incubated for 1.5-2 hours in staining solution II (0.05% aniline blue =methyl blue, 0.067 M di-potassium hydrogen phosphate) and analyzed by microscopy immediately thereafter. LP) are used. After aniline blue staining, the spores appeared blue under UV light. The papillae could be recognized beneath the fungal appressorium by a green/yellow staining. The hypersensitive reaction (HR) was characterized by a whole cell fluorescence.

8.4 Evaluating the Susceptibility to Soybean Rust

Plants are screened macroscopically 14 days after inoculation.

Screening method:

The progression of the soybean rust disease was scored by the estimation of the diseased area (area which was covered by sporulating uredinia) on the backside (abaxial side) of the leaf. Additionally the yellowing of the leaf was taken into account. (for complete scheme see FIG. 7).

Results of Screening

The macroscopic disease symptoms of soybean against *P. pachyrhizi* of 17 independent events (To plants, 2-3 clones per event) were scored 14 days after inoculation. Clones from non-transgenic soybean plants were used as control. The average scoring of non-transgenic control plants was 4.07. After screening all plants, the average of the clones was calculated, which were derived from one event. For analysis of the effect the average of the controls was set to zero, and the average result of all clones from one event was subtracted from the control. Negative values show enhanced resistance, whereas positive values indicate enhanced susceptibility (FIG. 8). It was shown that the in planta expression of a RNAi construct targeting a steroyl-methyl transferase of *P. pachyrhizi* leads to a disease scoring of transgenic plants compared to non-transgenic controls. So, the expression of an RNAi construct targeting the SMT1 enzyme of *Phakopsora pachyrhizi* enhances the resistance of soybean against soybean rust.

The invention claimed is:

1. A method for producing a plant and/or a part thereof resistant to a fungus comprising:

a) providing a recombinant nucleic acid comprising a target nucleic acid that is identical and/or complementary to at least 19 contiguous nucleotides of a target sterol methyltransferase (SMT1)-gene, b) introducing said recombinant nucleic acid into a plant and/or part thereof, wherein said target SMT1-gene has at least 95% sequence identity to the nucleic acid sequence of SEQ ID NO: 1, SEQ ID NO: 2, or SEQ ID NO: 3.

2. The method of claim 1, wherein the recombinant nucleic acid provides for a dsRNA and/or a si-RNA in the plant, part thereof, and/or in a fungus infecting the plant or part thereof, once the recombinant nucleic acid is expressed, wherein at least 19 contiguous nucleotides of the dsRNA and/or the si-RNA are complementary to the target SMT1-gene.

3. The method of claim 1, wherein the target SMT-1 gene has the nucleic acid sequence of SEQ ID NO: 1, SEQ ID NO: 2, or SEQ ID NO: 3.

4. The method of claim 1, wherein the recombinant nucleic acid comprises:

a) a promoter that is functional in a plant cell, operably linked to a target nucleic acid which is identical and/or complementary to at least 19 contiguous nucleotides of the target SMT1-gene and which, when it is transcribed, generates RNA comprising a first strand having a sequence complementary to at least 19 contiguous nucleotides of the target SMT1-gene and a second strand having a sequence complementary to the first strand or parts thereof; and b) a terminator regulatory sequence.

5. The method of claim 1, wherein the recombinant nucleic acid comprises:

a) a promoter that is functional in a plant cell, operably linked to a target nucleic acid which, when it is transcribed, generates RNA comprising a first strand having a sequence identical or complementary to at least 19 contiguous nucleotides of the target SMT1-gene; and b) a terminator regulatory sequence.

6. The method of claim 1, wherein the target nucleic acid comprises 19 to 500 nucleotides.

7. The method of claim 6, wherein the target nucleic acid comprises 250 to 350 nucleotides.

8. The method of claim 1, wherein the target nucleic acid is identical and/or complementary to at least 19 contiguous nucleotides of the target SMT1-gene.

9. The method of claim 1, wherein 19 to 24 contiguous nucleotides of the target nucleic acid are identical and/or complementary to the target SMT1-gene, and the remaining nucleotides of the target nucleic acid are not identical and/or complementary to the target SMT1-gene.

10. The method of claim 1, wherein the fungus is a hemibiotrophic fungus.

11. The method of claim 1, wherein the fungus is a soybean rust pathogen.

12. The method of claim 11, where the soybean rust pathogen is *Phakopsora meibomiae* and/or *Phakopsora pachyrhizi*.

13. A vector construct comprising a recombinant nucleic acid comprising:

a) a promoter that is functional in a plant cell, operably linked to a target nucleic acid which is identical and/or complementary to at least 19 contiguous nucleotides of a target sterol methyltransferase (SMT1)-gene; and b) a terminator regulatory sequence, wherein said target SMT1-gene has at least 95% sequence identity to the nucleic acid sequence of SEQ ID NO: 1, SEQ ID NO: 2, or SEQ ID NO: 3.

14. The vector construct of claim 13, wherein the target nucleic acid, when it is transcribed, generates RNA comprising a first strand having a sequence complementary to at least 19 contiguous nucleotides of the target SMT1-gene, and a second strand having a sequence complementary to the first strand or parts thereof.

15. The vector construct of claim 13, wherein the target nucleic acid, when it is transcribed, generates RNA comprising a first strand having a sequence complementary or identical to at least 19 contiguous nucleotides of the target SMT1-gene.

16. The vector construct of claim 13, wherein the target nucleic acid comprises 19 to 500 nucleotides.

17. The vector construct of claim 13, wherein the promoter is a constitutive, inducible, pathogen-inducible, developmental stage-preferred, cell type-preferred, tissue-preferred and/or organ-preferred promoter.

18. A transgenic plant cell comprising a recombinant nucleic acid comprising a target nucleic acid which is identical and/or complementary to at least 19 contiguous nucleotides of a target sterol methyltransferase (SMT1)-gene, wherein said target SMT1-gene has at least 95% sequence identity to the nucleic acid sequence of SEQ ID NO: 1, SEQ ID NO: 2, or SEQ ID NO: 3.

19. The transgenic plant cell of claim 18, wherein the target SMT1-gene has the nucleic acid sequence of SEQ ID NO: 1, SEQ ID NO: 2, or SEQ ID NO: 3.

20. The transgenic plant cell of claim 18, wherein the recombinant nucleic acid provides for a dsRNA and/or a si-RNA in a plant, part thereof, and/or in a fungus infecting the plant or part thereof, once the recombinant nucleic acid is expressed.

21. The transgenic plant cell of claim 18, wherein the recombinant nucleic acid comprises:

a) a promoter that is functional in the plant cell and operably linked to the target nucleic acid; and b) a terminator regulatory sequence, and wherein the target nucleic acid, when it is transcribed, generates RNA comprising a first strand having a sequence complementary to at least 19 contiguous nucleotides of the target SMT1-gene and a second strand having a sequence complementary to the first strand or parts thereof.

22. The transgenic plant cell of claim 18, wherein the recombinant nucleic acid comprises:

a) a promoter that is functional in the plant cell and operably linked to the target nucleic acid; and b) a terminator regulatory sequence, wherein the target nucleic acid, when it is transcribed, generates RNA comprising a first strand having a sequence complementary or identical to at least 19 contiguous nucleotides of the target SMT1-gene.

23. The transgenic plant cell of claim 18, wherein the promoter is a constitutive, inducible, pathogen-inducible, developmental stage-preferred, cell type-preferred, tissue-preferred, and/or organ-preferred promoter.

24. The transgenic plant cell of claim 18, wherein the plant cell is from a legume.

25. The transgenic plant cell of claim 24, wherein the plant cell is from a plant selected from the group consisting of beans, soya, pea, clover, kudzu, lucerne, lentils, lupins, vetches, and groundnut.

26. A transgenic plant or part thereof comprising the transgenic plant cell of claim 18 or consisting of said cells.

27. A transgenic seed derived from the plant of claim 26.

* * * * *